(12) United States Patent
Goldenberg et al.

(10) Patent No.: US 12,268,632 B2
(45) Date of Patent: *Apr. 8, 2025

(54) SELF-RETAINING IMPLANTABLE DRUG DELIVERY DEVICE

(71) Applicant: GoldenBiotech, LLC, Newbury Park, CA (US)

(72) Inventors: Merrill Goldenberg, Newbury Park, CA (US); Steven H. Rauchman, Mission Hills, CA (US)

(73) Assignee: GoldenBiotech, LLC, Newbury Park, CA (US)

( * ) Notice: Subject to any disclaimer, the term of this patent is extended or adjusted under 35 U.S.C. 154(b) by 868 days.

This patent is subject to a terminal disclaimer.

(21) Appl. No.: 16/411,111

(22) Filed: May 13, 2019

(65) Prior Publication Data

US 2020/0268554 A1    Aug. 27, 2020

Related U.S. Application Data

(60) Provisional application No. 62/714,383, filed on Aug. 3, 2018, provisional application No. 62/670,766, filed on May 12, 2018.

(51) Int. Cl.
| | | |
|---|---|---|
| *A61F 9/00* | (2006.01) | |
| *A61F 2/16* | (2006.01) | |
| *A61F 9/007* | (2006.01) | |
| *A61K 9/00* | (2006.01) | |
| *A61K 47/34* | (2017.01) | |

(52) U.S. Cl.
CPC ............. *A61F 9/0017* (2013.01); *A61F 2/16* (2013.01); *A61F 9/00781* (2013.01); *A61K 9/0087* (2013.01); *A61K 47/34* (2013.01); *A61F 2250/0067* (2013.01)

(58) Field of Classification Search
CPC ...... A61F 9/0017; A61F 2/16; A61F 9/00781; A61F 2250/0067; A61K 9/0087; A61K 47/34

See application file for complete search history.

(56) References Cited

U.S. PATENT DOCUMENTS

| | | |
|---|---|---|
| 5,378,475 A | 3/1995 | Smith et al. |
| 5,395,618 A | 3/1995 | Darougar et al. |
| 6,152,916 A | 11/2000 | Bige |
| 6,299,604 B1 | 10/2001 | Ragheb et al. |
| 10,004,636 B2 | 6/2018 | Alster et al. |
| 2006/0020253 A1 | 1/2006 | Prescott |
| 2006/0110428 A1 | 5/2006 | deJuan et al. |
| 2006/0111791 A1 | 5/2006 | Forsell |
| 2006/0200097 A1 | 9/2006 | Humayun et al. |
| 2008/0311191 A1* | 12/2008 | Nangia ............... A61K 31/522 424/463 |
| 2009/0196903 A1 | 8/2009 | Kliman |
| 2014/0303544 A1 | 10/2014 | Haffner et al. |
| 2015/0133546 A1* | 5/2015 | Butuner ............... A61K 45/06 514/530 |
| 2015/0342894 A1* | 12/2015 | Anderson ........... A61K 9/0092 424/490 |
| 2016/0166430 A1 | 6/2016 | Jain et al. |
| 2018/0333296 A1 | 11/2018 | Heitzmann et al. |

FOREIGN PATENT DOCUMENTS

WO    2007083293 A1    7/2007

OTHER PUBLICATIONS

Anonymous, Dextenza Brochure, p. 3 (2018).
Anonymous, SRS II Self-Retaining Bicanaliculus Intubation Sett II Brochure, p. 2 (2018).
Blizzard, et al., Pharmacokinetic Studies of Sustained-Release Depot of Dexamethasone in Beagle Dogs, J. Ocular Pharmacol Ther. 32(9): 595-600 (2016).
Gira, et al., Evaluating the Patient Experience after Implantation of a 0.4 mg Sustained Release Dexamethasone Intracanalicular Insert (Dextenza™): Results of a Qualitative Survey, Patient Prefer. Adherence 11: 487-494 (2017).
WIPO, OCT Form ISA 210, International Search Report of PCT/US2019/032067, mailed Sep. 16, 2019.
WIPO, OCT Form ISA 237, Written Opinion of PCT/US2019/032067, mailed Sep. 16, 2019.

* cited by examiner

*Primary Examiner* — Robert A Wax
*Assistant Examiner* — Olga V. Tcherkasskaya
(74) *Attorney, Agent, or Firm* — UltimatEdge IP Law Group, P.C.; Dean G. Stathakis

(57) ABSTRACT

Disclosed herein is a medical device for extended release of drugs. The device comprises a stent embedded with one or more drug depots that release of a therapeutic agent in a controlled manner. Each end of the stent may contain one or more anchors or attachment points which enable self-retention of the medical device once properly placed. The disclosed device further comprises a biosensor to monitor physiological characteristics like, e.g., intraocular pressure (IOP).

19 Claims, 14 Drawing Sheets

SELF-RETAINING IMPLANTABLE DRUG DELIVERY DEVICE

This application claims the benefit of priority and the filing date pursuant to 35 U.S.C. § 119(e) to U.S. Provisional Patent Application 62/670,766, filed May 12, 2018, and U.S. Provisional Patent Application 62/714,383, filed Aug. 3, 2018, the entire content of each of which is hereby incorporated by reference in its entirety.

Theoretically, implantable drug delivery devices can locally or systemically deliver a therapeutic agent from the vicinity that it is placed in a controlled manner. One key advantage of this controlled release is that it inherently improves efficacy of the treatment and decreases potential side effects, when compared to other routes of administration such as oral, rectal, topical, or systemic. Nonetheless, a problem with the known implantable drug delivery devices is that the delivery rate cannot be controlled during all operational phases of the devices (i.e., drug delivery rates may change thereby resulting in, for example, first order delivery kinetics or second order delivery kinetics). Such problems result in a drug delivery device that administers drugs in an unpredictable pattern, thereby resulting in poor therapeutic benefit. As such, there is a need for a drug delivery device, which can be optimized to deliver any therapeutic, diagnostic, or prophylactic agent for any time period up to several years maintaining a controlled and desired rate.

Ideal delivery of drugs from an implantable drug delivery device would follow "zero order kinetics. Zero-order release kinetics refers to the process of constant drug release from a drug delivery device resulting in drug blood levels that would remain constant throughout the delivery period. Furthermore, an implantable drug delivery device should be non-invasive to eliminate the risks of surgery, and have the ability to be removed when the loaded drug depot is spent or unwanted and unexpected side effects or complications occur.

The disclosed implantable drug delivery device is well suited to address the above-mentioned problems.

SUMMARY

Aspects of the present specification disclose a self-retaining implantable drug delivery device which provides for controlled release of a therapeutic agent over an extended period of time. The disclosed implantable drug delivery device comprises a stent portion made of medical grade silicone which forms a semi-rigid cylindrical tube having a first distal end and a second distal end and an elongated body between the first distal end and the second distal end. The central portion of the elongated body of the stent comprises one or more silicone embedded controlled-release drug depots comprising one or more therapeutic drugs. The drug depot comprises biocompatible a polymer matrix that allows for slow and extended release of a therapeutic agent. Each end of the implantable drug delivery device may optionally contain anchors or attachment points that facilitate self-retention of the stent once positioned in place. The one or more controlled-release drug depots may be coated with a thin layer of a metal or other polymer material that appropriately controls the release of one or more therapeutic drugs. The stent can be designed to contain more than one silicone embedded drug depot, each containing the same or different therapeutic agent. The one or more therapeutic agents can be released simultaneously with each depot having its own release rate or sequentially with each depot having its own release rate.

Aspects of the present specification disclose a self-retaining canalicular device which provides for controlled release of a therapeutic agent over an extended period of time. The disclosed implantable drug delivery device comprises a stent portion made of medical grade silicone which forms a semi-rigid cylindrical tube having a first distal end and a second distal end and an elongated body between the first distal end and the second distal end. The central portion of the elongated body of the self-retaining canalicular device comprises one or more silicone embedded controlled-release drug depots comprising one or more therapeutic drugs. The drug depot comprises biocompatible a polymer matrix that allows for slow and extended release of a therapeutic agent. Each end of the self-retaining canalicular device may optionally contain anchors or attachment points that facilitate self-retention of the stent once positioned in place. The one or more controlled-release drug depots may be coated with a thin layer of a metal or other polymer material that appropriately controls the release of one or more therapeutic drugs. The self-retaining canalicular device can be designed to contain more than one silicone embedded drug depot, each containing the same or different therapeutic agent. The one or more therapeutic agents can be released simultaneously with each depot having its own release rate or sequentially with each depot having its own release rate. When properly positioned in patient, the majority of the self-retaining canalicular device resides within the canaliculus with a small loop portion of the stent comprising one or more controlled-release drug depots in contact with the front of the eye. The first and the second distal ends are located in the lumen of a lacrimal sac, secured in place by the anchors or attachment points. The self-retaining canalicular device may further comprise additional anchors or attachment points placed near the end of stent to allow for additional fixation points if the stent is too lax. The self-retaining canalicular device may further comprise a biosensor capable of detecting and monitoring properties of a bodily fluid from the eye (e.g., tear fluid) and/or intraocular pressure (IOP). The approximate dimensions of the stent may be about 0.6 mm outside diameter, about 0.3 mm inside diameter and about 30 mm length.

Aspects of the present specification disclose a self-retaining canalicular device which provides for extended release of a therapeutic agent to a lacrimal sac as well as intubation of a canaliculus. The disclosed self-retaining canalicular device comprises a stent made of medical grade silicone which forms a semi-rigid cylindrical tube having a first distal end and a second distal end and an elongated body between the first distal end and the second distal end. One or more controlled-release drug depots disclosed herein are embedded at or near the first distal end, the second distal end, or both the first and the second distal end. Each end of the stent may optionally contain one or more anchors or attachment points that facilitate self-retention of the stent once positioned in place. The one or more controlled-release drug depots may be coated with a thin layer of a metal or other material that appropriately controls the release of one or more therapeutic drugs to a lacrimal sac. The self-retaining canalicular device can be designed to contain more than one silicone embedded drug depot, each containing the same or different therapeutic agent. The one or more therapeutic agents can be released simultaneously with each depot having its own release rate or sequentially with each depot having its own release rate. When properly positioned in the patient, the majority of the stent resides within the canaliculus with a small loop portion in contact with the front of the eye. The first and the second distal ends comprising one or more controlled-release drug depots are located in the lumen of a lacrimal sac, secured in place by the anchors or attachment points. The self-retaining canalicular device may further comprise additional anchors or attachment points placed near the end of stent to allow for additional fixation points if the stent is too lax. The stent may further comprise a biosensor capable of detecting and monitoring properties of a bodily fluid from the eye (e.g., tear fluid) and/or intraocular pressure (IOP).

Aspects of the present specification disclose a kit. A kit disclosed herein comprising a self-retaining canaliculus device disclosed herein as well as metallic stylets that insert near distal end of tube to facilitate insertion and placement of stent, and which are withdrawn after insertion.

BRIEF DESCRIPTION OF THE DRAWINGS

FIGS. 2C-D showing placement of a unicanalicular stent using anchors comprising flexible winglets; FIGS. 2E-F showing placement of a bicanalicular stent using attachment points comprising a magnetic connector.

FIG. 4B showing a bicanalicular stent with a first and second distal ends, the first and the second distal ends comprising first and second connection points, an elongated body and one or more drug depots comprising one or more therapeutic drugs centrally located with respect to the elongated body; FIG. 4C showing a bicanalicular stent with a first and second distal ends, the first or the second distal end comprising one or more anchors, an elongated body and one or more drug depots comprising one or more therapeutic drugs centrally located with respect to the elongated body; FIG. 4D showing a bicanalicular stent with a first and second distal ends, the first and the second distal end comprising one or more anchors, an elongated body and one or more drug depots comprising one or more therapeutic drugs centrally located with respect to the elongated body; FIG. 4E showing a bicanalicular stent with a first and second distal ends, the first or second distal end comprising a plurality of anchors, an elongated body and one or more drug depots comprising one or more therapeutic drugs centrally located with respect to the elongated body; FIG. 4F showing a unicanalicular stent with a first and second distal ends, an elongated body and one or more drug depots comprising one or more therapeutic drugs centrally located at either the first or the second distal end; FIG. 4G showing a unicanalicular stent with a first and second distal ends, the first distal end comprising one or more anchors, an elongated body and one or more drug depots comprising one or more therapeutic drugs located at the second distal end; and FIG. 4H showing a unicanalicular stent with a first and second distal ends, the first distal end comprising a plurality of anchors, an elongated body and one or more drug depots comprising one or more therapeutic drugs located at the second distal end; and FIG. 4I showing a bicanalicular stent with a first and a second distal ends, the first and second distal ends comprising a plurality of anchors, an elongated body and one or more drug depots comprising one or more therapeutic drugs centrally located with respect to the elongated body.

DETAILED DESCRIPTION

The present specification discloses a self-retaining implantable drug delivery device for the controlled release of a therapeutic agent. A self-retaining implantable drug delivery device disclosed herein can be easily inserted into a lumen of a vessel or duct during placement, adequately secured once proper placement is achieved and designed for easy removal when desired. Although the disclosed self-retaining implantable drug delivery device can be placed in any vessel or duct of an organ or other bodily part, e.g., the brain, heart, pancreas and the like) in order to exert a therapeutic effect, a self-retaining implantable drug delivery device disclosed herein will be exemplified using topical delivery of a therapeutic agent to the eye to treat glaucoma.

Figure 1:
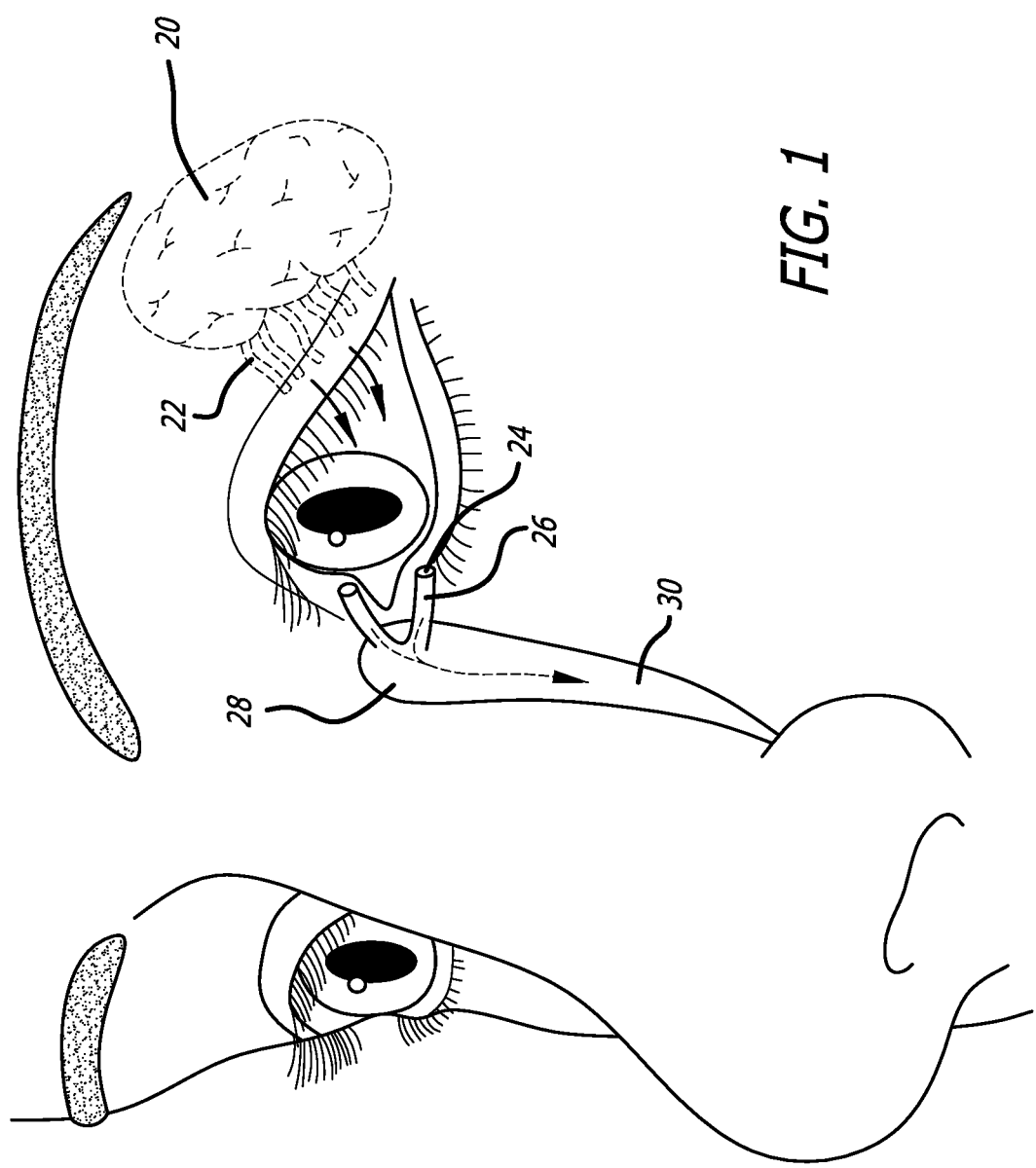
FIG. 1 shows the anatomical features of the lacrimal drainage system of the eye.

Referring to FIG. 1, the lacrimal drainage system of an eye includes lacrimal gland 20 with associated excretory ducts 22, inferior and superior lacrimal puncta 24, inferior and superior lacrimal canaliculi 26, lacrimal sac 28 and nasolacrimal duct 30. Lacrimal gland 20 secretes lacrimal fluid (tears) through its excretory ducts 22, which convey the fluid to the surface of the human eye. The lacrimal fluid collects at the medial canthal angle, where it drains into the inferior puncta 24 of the lower eyelid and the superior puncta 24 of the upper lids. Each punctum 24 is a small oval opening approximately 0.3 mm in diameter that is located at the summit of an elevated papilla. From each punctum 24 the canaliculus 26 (inferior and superior canaliculus) passes first vertically for about 2 mm and then turns sharply to run medially for about 8 mm. At the angle, a slight dilation, the ampulla is present. The canaliculi 26 converges towards lacrimal sac 28. Lacrimal sac 28 occupies a fossa formed by the maxillary and lacrimal bones. It measures 1.5 mm to 2.5 mm in diameter and approximately 12 mm to 15 mm in vertical length. From lacrimal sac 28 the lacrimal fluid drains into the nasolacrimal duct 30, which extends for about 15 mm, passing through a bony canal in the maxillary bone, to an opening in the nose beneath the inferior nasal turbinate.

As described herein, in one embodiment, the present specification discloses self-retaining implantable drug delivery device which provides for extended release of a therapeutic agent as well as intubation of a lacrimal canaliculus. Importantly, the disclosed canalicular device provides several advantages over the current depot-delivery systems that are under development. For example, punctal plugs with sustained released prostaglandin analogues have been in development for quite some time. Problems with silicone puntal plugs include a limited surface area exposed to tear film and limited volume. In addition, punctal plugs tend to fall out in high frequency and this happens without patient awareness. Thus, patient would be denied therapeutic benefit of drug for extended period of time (until next doctor visit). Plugs are also designed to prevent tear egress from punta in patients with dry eyes. Punctal plugs can actually induce tearing in patients with normal tear production. Punctal plugs only contain sufficient surface area for a single drug. Approximately 50% of all patients with chronic open angle glaucoma require more than one drug for adequate IOP control. Extended use of punctal plugs (which would be required to treat glaucoma) are known to damage the punta and cause scarring. By comparison, a canalicular stent disclosed herein has sufficient volume for two drugs. Additionally, the interface of the external tube against tear film and mucosa actually facilitates transport of tears distally and this maintains normal physiological function of system. Finally, if a canalicular stent disclosed herein extrudes, the patient will become symptomatic (local irritation) and stent can be removed and replaced promptly.

Figure 3:
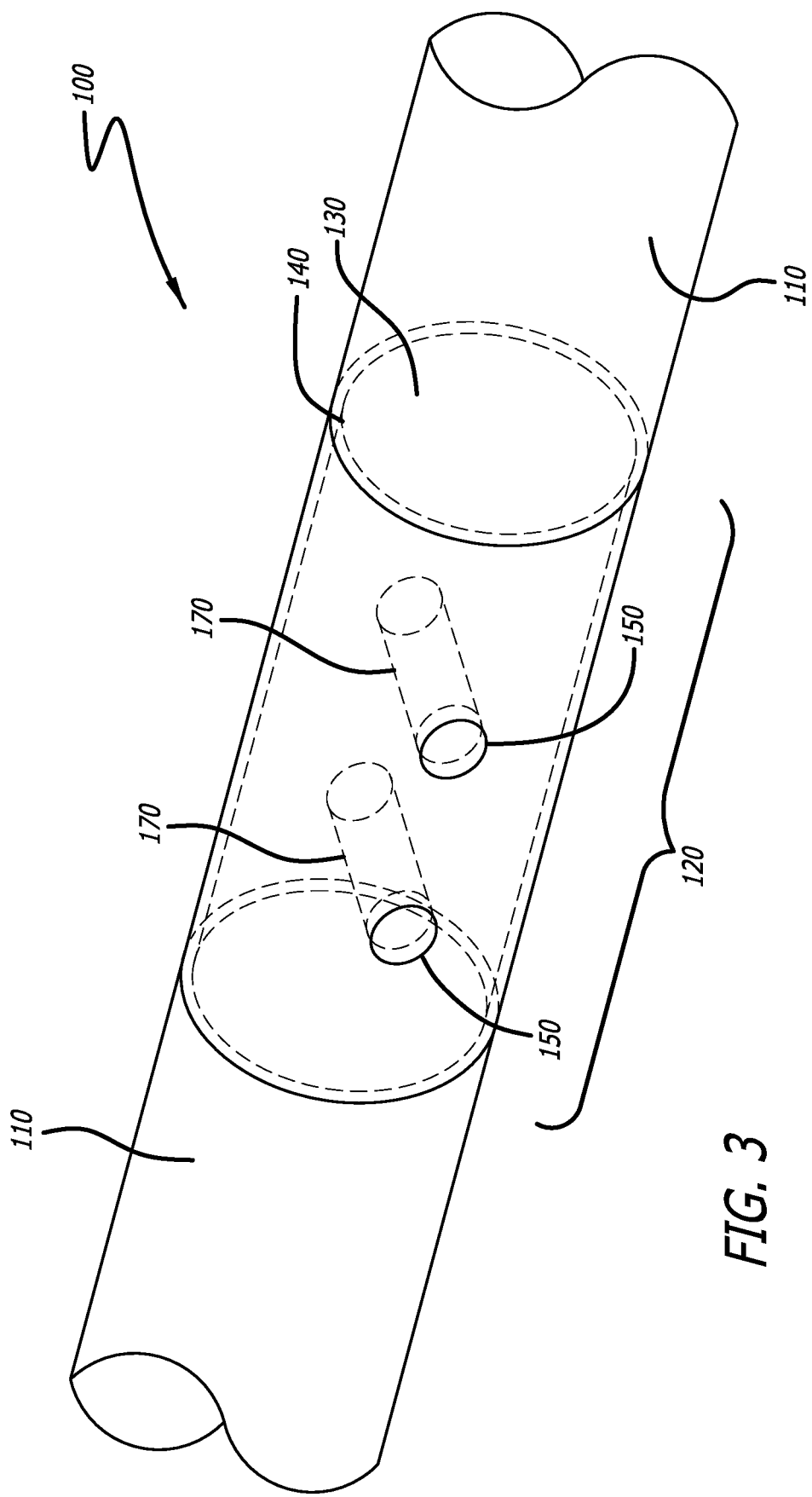
FIG. 3 shows a perspective view of a portion of a self-retaining implantable drug delivery device disclosed herein illustrating drug depot comprising a coated polymer matrix with two depot channels.

Referring to FIGS. 3-4, a self-retaining implantable drug delivery device 100 disclosed herein comprises a stent portion 110, one or more drug depots 120, and one or more anchors 180 and/or one or more attachment points 190. Referring to FIG. 3, drug depot 120 comprises a polymer matrix 130 and a coating layer 140. In addition, drug depot 120 includes one or more openings, which is FIG. 3 is shown as depot channels 150.

Aspects of the present specification disclose a stent portion (or stent) 110. A stent portion 110 of a self-retaining implantable drug delivery device 100 disclosed herein is a metal or plastic tube inserted into the lumen of an anatomic vessel or duct to keep the passageway open. A stent 110 can be non-expandable, thus having a fixed diameter or expandable allowing the diameter of the stent portion to be adjusted for more secure and/or proper positioning and/or improved function of the stent portion in the lumen. A stent 110 disclosed herein can be a solid (non-tubular) structure, a tubular structure with a lumen, or a mesh structure. The use of a particular type of stent is typically dictated based on the medical outcome trying to be achieved. For example, an expandable stent is typically used coronary, vascular and biliary procedures. In the other hand, a fixed stent can be used in allow the flow of urine between kidney and bladder or lacrimal fluid from the eye to the nasal cavity.

In one embodiment, a self-retaining implantable drug delivery device 100 disclosed herein comprises a stent portion 110 having a first distal end, a second distal end and an elongated body between the first distal end and the second distal end. An elongated body disclosed herein has an outer diameter if solid, and an outer and inner diameter if tubular. In aspects of this embodiment, an elongated body of a solid or tubular stent disclosed herein has an outer diameter of, e.g., about 1 mm, about 2 mm, about 3 mm, about 4 mm, or about 5 mm. In other aspects of this embodiment, an elongated body of a solid or tubular stent disclosed herein has an outer diameter of, e.g., at least 1 mm, at least 2 mm, at least 3 mm, at least 4 mm, or at least 5 mm. In yet other aspects of this embodiment, an elongated body of a solid or tubular stent disclosed herein has an outer diameter of, e.g., at most 1 mm, at most 2 mm, at most 3 mm, at most 4 mm, or at most 5 mm. In yet other aspects of this embodiment, an elongated body of a solid or tubular stent disclosed herein has an outer diameter of, e.g., about 1 mm to about 2 mm, about 1 mm to about 3 mm, about 1 mm to about 4 mm, about 1 mm to about 5 mm, about 2 mm to about 3 mm, about 2 mm to about 4 mm, about 2 mm to about 5 mm, about 3 mm to about 4 mm, about 3 mm to about 5 mm, or about 3 mm to about 5 mm. In other aspects of this embodiment, an elongated body of a solid or tubular stent disclosed herein has an outer diameter of, e.g., about 0.3 mm to about 1 mm, about 0.4 mm to about 0.7 mm, about 0.4 mm to about 0.8 mm, about 0.5 mm to about 0.9 mm, about 0.6 mm to about 1 mm, about 0.3 mm to about 0.5 mm, about 0.4 mm to about 0.6 mm, about 0.5 mm to about 0.7 mm, about 0.6 mm to about 0.8 mm, about 0.7 mm to about 0.9 mm, or about 0.8 mm to about 1 mm.

In aspects of this embodiment, an elongated body of a tubular stent disclosed herein has an inside diameter of, e.g., about 0.25 mm, about 0.5 mm, about 0.75 mm, about 1 mm, about 2 mm, about 3 mm, or about 4 mm. In other aspects of this embodiment, an elongated body of a solid or tubular stent disclosed herein has an outer diameter of, e.g., at least 0.25 mm, at least 0.5 mm, at least 0.75 mm, at least 1 mm, at least 2 mm, at least 3 mm, or at least 4 mm. In yet other aspects of this embodiment, an elongated body of a tubular stent disclosed herein has an inside diameter of, e.g., at most 0.25 mm, at most 0.5 mm, at most 0.75 mm, at most 1 mm, at most 2 mm, at most 3 mm, or at most 4 mm. In yet other aspects of this embodiment, an elongated body of a tubular stent disclosed herein has an inside diameter of, e.g., about 0.25 mm to about 1 mm, about 0.25 mm to about 2 mm, about 0.25 mm to about 3 mm, about 0.25 mm to about 4 mm, about 0.5 mm to about 1 mm, about 0.5 mm to about 2 mm, about 0.5 mm to about 3 mm, about 0.5 mm to about 4 mm, about 0.75 mm to about 1 mm, about 0.75 mm to about 2 mm, about 0.75 mm to about 3 mm, about 0.75 mm to about 4 mm, about 1 mm to about 2 mm, about 1 mm to about 3 mm, or about 1 mm to about 4 mm. In other aspects of this embodiment, an elongated body of a tubular stent disclosed herein has an inside diameter of, e.g., diameter of about 0.1 mm to about 0.5 mm, about 0.2 mm to about 0.6 mm, about 0.1 mm to about 0.3 mm, about 0.2 mm to about 0.4 mm, about 0.4 mm to about 0.5 mm, or about 0.4 mm to about 0.6 mm.

An elongated body of a stent portion disclosed herein can be of any length as long as the length suitable to deliver a controlled release of one or more therapeutic drugs and is properly secured in lumen. In another embodiment, an elongated body of a canalicular stent disclosed herein has a length suitable to deliver a controlled release of one or more therapeutic drugs, is properly secured in lumen, and properly intubates a vessel or duct to keep the passageway open. Intubation is meant to include the insertion of a self-retaining implantable drug delivery device disclosed herein comprising either a tubular or solid (non-tubular) stent into a lumen in order to keep a passageway open regardless of whether fluid flow through a tubular stent or around a solid stent.

In aspects of this embodiment, a self-retaining implantable drug delivery device disclosed herein has a length of about 10 mm to about 50 mm, about 10 mm to about 30 mm, about 20 mm to about 40 mm, or about 30 mm to about 50 mm. In other aspects of this embodiment, a self-retaining implantable drug delivery device disclosed herein has a length of about 5 mm to about 20 mm, about 7 mm to about 15 mm, or about 10 mm to about 12 mm.

In one embodiment, a self-retaining implantable drug delivery device disclosed herein is designed to be inserted into a lacrimal canaliculus (FIG. 2A-F). Such a canalicular stent disclosed herein can be a unicanalicular stent (FIG. 4F-H) or a bicanalicular stent (FIGS. 4A-E and I). A canalicular stent disclosed herein is not a plug, such as, e.g., a punctal plug. In aspects of this embodiment, an elongated body of a bicanalicular stent disclosed herein has a length of about 10 mm to about 50 mm, about 10 mm to about 30 mm, about 20 mm to about 40 mm, or about 30 mm to about 50 mm. In other aspects of this embodiment, an elongated body of a unicanalicular stent disclosed herein has a length of about 5 mm to about 20 mm, about 7 mm to about 15 mm, or about 10 mm to about 12 mm.

A self-retaining implantable drug delivery device disclosed herein is self-retaining. Self-retention maintains the desired position of a self-retaining implantable drug delivery device disclosed herein in the lumen of a vessel or duct and can also prevent a self-retaining implantable drug delivery device from extruding from a vessel or duct or otherwise losing its desired position.

Self-retention of a medical device disclosed herein can be achieved by one or more attachment points 190 and/or one or more anchors 180. An attachment point 190 disclosed herein can be a coupling mechanism that connects the first and second distal ends of a self-retaining implantable drug delivery device disclosed herein. Non-limiting examples of one or more attachment points 190 include a pair of hooks, a hook and eyelet pair, Velcro, male and female connectors, and magnetic connectors. In one embodiment after a self-retaining implantable drug delivery device disclosed herein is a bicanalicular stent positioned so that both the first and second distal ends of a stent are located within a lacrimal sac, the first and second distal ends can be connected to form a loop and the bicanalicular stent now forming a circle (see FIG. 2E-F).

An attachment point can also be a coupling device that connects the first or second distal ends of a self-retaining implantable drug delivery device disclosed herein to a body portion of an individual who is having a self-retaining implantable drug delivery device disclosed herein implanted or otherwise positioned in a vessel or duct. In one embodiment, a self-retaining implantable drug delivery device is a unicanicular stent disclosed herein comprises one or more drug depots at either the first or second distal end where the drug depot disclosed herein further comprises iron. Such a unicanalicular stent can be coupled to a body portion treated with a magnetic coating applied to the skin or other body part in the vicinity of the punctum where the self-retaining implantable drug delivery device comprising the iron is positioned.

Figure 4A:
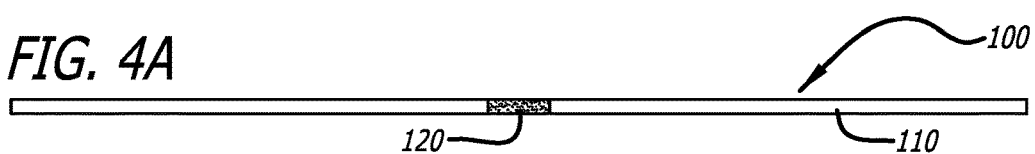
FIGS. 4A-4I is a schematic depicting various embodiments of a self-retaining implantable drug delivery device disclosed herein with FIG. 4A showing a bicanalicular stent with a first and second distal ends, an elongated body and one or more drug depots comprising one or more therapeutic drugs centrally located with respect to the elongated body.
Figure 4B:
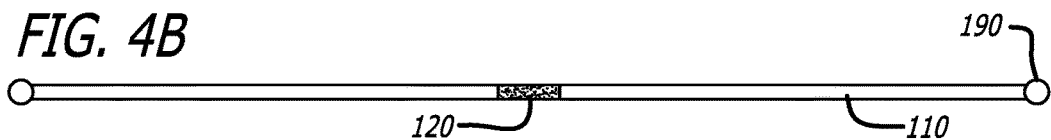
Figure 4C:
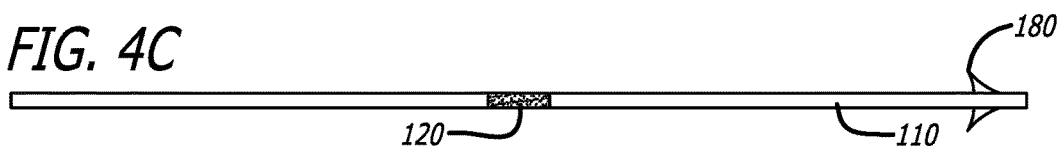
Figure 4D:
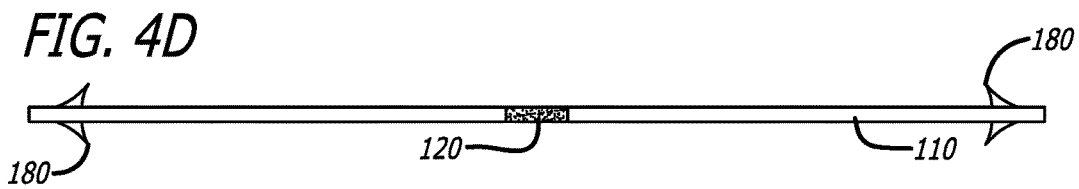
Figure 4E:
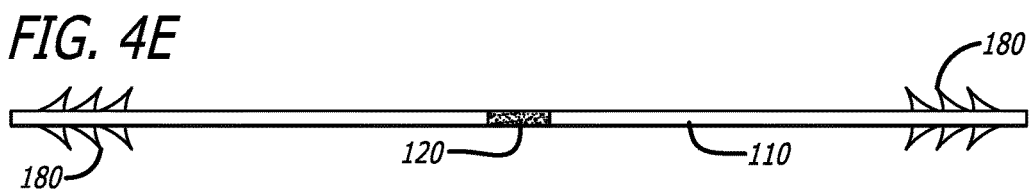
Figure 4F:
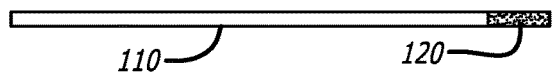
Figure 4G:
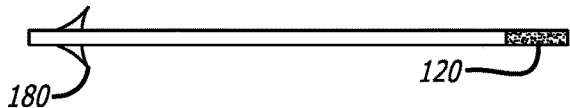
Figure 4H:
Figure 4I:
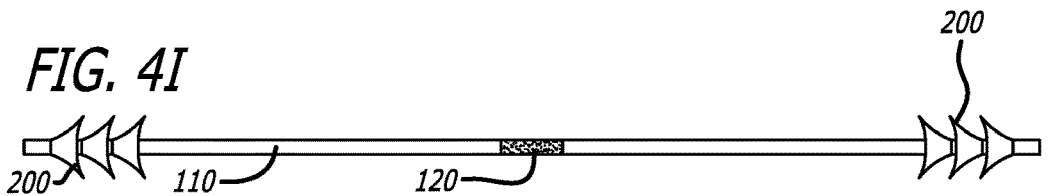

An anchor 180 can be a device that fixes the position of a self-retaining implantable drug delivery device disclosed herein in place using a mechanical force. Non-limiting examples of one or more anchors include a flexible winglet (FIGS. 4B-E, H and I). A flexible winglet can be barbed-like, occupying only a region of a stent portion (FIGS. 4B-E, H), or be conical, circumscribing the entire circumference of a stent (FIG. 4I).

In one embodiment, a self-retaining implantable drug delivery device disclosed herein has a stent portion having an elongated body comprises one or more flexible winglets that anchor a self-retaining implantable drug delivery device disclosed herein in place. In aspects of this embodiment, one or more flexible winglets are located at a first distal end of an elongated body, a second distal end of an elongated body, or both a first and a second distal end of an elongated body of a stent portion disclosed herein. Placement of one or more flexible winglets at the first and/or second distal end enables self-retention of a self-retaining implantable drug delivery device disclosed herein once the winglets are properly placed in a vessel or duct. For example, with respect to a canicular stent, the one or more flexible winglets fold inward during insertion through the puctum and caniculus for easy insertion, but one this distal end enters into a lacrimal sac, the one or more winglets flare out in a manner that prevents a canalicular stent disclosed herein from retreating back into the caniculus.

In one embodiment, a single flexible winglet is located at a first distal end of an elongated body, a second distal end of an elongated body, or both a first and a second distal end of an elongated body of a stent portion of a self-retaining implantable drug delivery device disclosed herein. In another embodiment, a plurality of flexible winglets is located at a first distal end of an elongated body, a second distal end of an elongated body, or both a first and a second distal end of an elongated body of a stent portion of a self-retaining implantable drug delivery device disclosed herein. The plurality of flexible winglets disclosed herein can be arranged in succession as a series starting from a distal end and then at positions proximally to the initial flexible winglet along the length of the elongated body. In this way, a self-retaining implantable drug delivery device disclosed herein can be more securely placed based on the anatomy and physical characteristics of a vessel or duct for which the self-retaining implantable drug delivery device is being secured. For example, a self-retaining implantable drug delivery device disclosed herein, like a canalicular stent disclosed herein, can be positioned more securely by inserting the stent deeper into a canaliculus so that one or more of the plurality of flexible winglets are inserted into a lacrimal sac until the desired position of a canalicular stent is achieved. In this manner, the plurality of flexible winglets ensures that the desired tension of a canalicular stent disclosed herein is maintained thereby ensuring that the stent remains in its desired position.

A flexible winglet disclosed herein can be of any size so long as a self-retaining implantable drug delivery device disclosed herein can be easily inserted through a lumen of a vessel or duct during placement adequately secures a self-retaining implantable drug delivery device disclosed herein once proper placement is achieved and enables for easy removal of a self-retaining implantable drug delivery device disclosed herein when desired. In aspects of this embodiment, a flexible winglet disclosed herein has a length of, e.g., about 0.5 mm, about 1.0 mm, about 1.5 mm, about 2.0 mm, about 2.5 mm, about 3.0 mm, or about 4.0 mm. In other aspects of this embodiment, a flexible winglet disclosed herein has a length of, e.g., about at least 0.5 mm, at least 1.0 mm, at least 1.5 mm, at least 2.0 mm, at least 2.5 mm, at least 3.0 mm, or at least 4.0 mm. In yet other aspects of this embodiment, a flexible winglet disclosed herein has a length of, e.g., at most 0.5 mm, at most 1.0 mm, at most 1.5 mm, at most 2.0 mm, at most 2.5 mm, at most 3.0 mm, or at most 4.0 mm. In yet other aspects of this embodiment, a flexible winglet disclosed herein has a length of, e.g., about 0.5 mm to about 1.0 mm, about 0.5 mm to about 2.0 mm, about 0.5 mm to about 3.0 mm, about 0.5 mm to about 4.0 mm, about 1.0 mm to about 2.0 mm, about 1.0 mm to about 3.0 mm, about 1.0 mm to about 4.0 mm, about 2.0 mm to about 3.0 mm, about 2.0 mm to about 4.0 mm, or about 3.0 mm to about 4.0 mm.

Aspects of the present specification disclose a drug depot. A drug depot disclosed herein comprises a polymer matrix, a coating layer and one or more therapeutic agents. A self-retaining implantable drug delivery device disclosed herein can comprise one or more drug depots disclosed herein. One or more drug depots are placed or embedded in one or more locations on a self-retaining implantable drug delivery device disclosed herein. In aspects of this embodiment, a self-retaining implantable drug delivery device disclosed herein comprises 1, 2, 3, 4, or 5 drug depots. In other aspects of this embodiment, a self-retaining implantable drug delivery device disclosed herein comprises at least 1, at least 2, at least 3, at least 4, or at least 5 drug depots. In yet other aspects of this embodiment, a self-retaining implantable drug delivery device disclosed herein comprises at most 1, at most 2, at most 3, at most 4, or at most 5 drug depots. In still other aspects of this embodiment, a self-retaining implantable drug delivery device disclosed herein comprises about 1 to about 2, about 1 to about 3, about 1 to about 4, about 1 to about 5, about 2 to about 3, about 2 to about 4, about 2 to about 5, about 3 to about 4, about 3 to about 5, or about 4 to about 5, drug depots.

In one embodiment, one or more drug depots are positioned or embedded in a portion of an elongated body of a stent portion of a self-retaining implantable drug delivery device disclosed herein at a location the effectively delivers or administers the one or more therapeutic agents as desired. In another aspect of this embodiment, one or more drug depots disclosed herein are positioned or embedded in a centrally-located portion of the elongated body of a self-retaining implantable drug delivery device disclosed herein. In yet another aspect of this embodiment, one or more drug depots disclosed herein are positioned or embedded in a distally-located portion of the elongated body of a self-retaining implantable drug delivery device disclosed herein. In yet another aspect of this embodiment, one or more drug depots disclosed herein are positioned or embedded at a first distal end, a second distal end or both a first and second distal end of the elongated body of a self-retaining implantable drug delivery device disclosed herein.

In one embodiment, with reference to a canicular stent, one or more drug depots disclosed herein are positioned or embedded in a portion of the elongated body of a canalicular stent disclosed herein at a location the effectively delivers or administers the one or more therapeutic agents to an eye surface. In an aspect of this embodiment, one or more drug depots disclosed herein are positioned or embedded in a centrally-located portion of the elongated body of a canalicular stent disclosed herein.

In an aspect of this embodiment, with reference to a canicular stent, one or more drug depots disclosed herein are positioned or embedded in a portion of the elongated body of a canalicular stent disclosed herein at a location the effectively delivers or administers the one or more therapeutic agents to a nose. In another aspect of this embodiment, one or more drug depots disclosed herein are positioned or embedded in a portion of the elongated body of a canalicular stent disclosed herein at a location the effectively delivers or administers the one or more therapeutic agents to a lacrimal sac. In yet another aspect of this embodiment, one or more drug depots disclosed herein are positioned or embedded in a distally-located portion of the elongated body of a canalicular stent disclosed herein. In yet another aspect of this embodiment, one or more drug depots disclosed herein are positioned or embedded at a first distal end, a second distal end or both a first and second distal end of the elongated body of a canalicular stent disclosed herein.

A drug depot disclosed herein comprises one or more therapeutic agents. Typically, one or more therapeutic agents are loaded into the polymer matrix in an amount of 1% to 25% of the total weight of the polymer matric material. In aspects of this embodiment, one or more therapeutic agents are loaded into the polymer matrix in an amount of, e.g., about 1%, about 2.5%, about 5%, about 7.5%, about 10%, about 12.5%, about 15%, about 17.5%, about 20%, about 22.5% or about 25% of the total weight of the polymer matric material. In other aspects of this embodiment, one or more therapeutic agents are loaded into the polymer matrix in an amount of, e.g., at least 1%, at least 2.5%, at least 5%, at least 7.5%, at least 10%, at least 12.5%, at least 15%, at least 17.5%, at least 20%, at least 22.5% or at least 25% of the total weight of the polymer matric material. In yet other aspects of this embodiment, one or more therapeutic agents are loaded into the polymer matrix in an amount of, e.g., at least 1%, at most 2.5%, at most 5%, at most 7.5%, at most 10%, at most 12.5%, at most 15%, at most 17.5%, at most 20%, at most 22.5% or at most 25% of the total weight of the polymer matric material. In still other aspects of this embodiment, one or more therapeutic agents are loaded into the polymer matrix in an amount of, e.g., about 1% to about 2.5%, about 1% to about 5%, about 1% to about 7.5%, about 1% to about 10%, about 1% to about 12.5%, about 1% to about 15%, about 1% to about 17.5%, about 1% to about 20%, about 1% to about 22.5%, about 1% to about 25%, about 2.5% to about 5%, about 2.5% to about 7.5%, about 2.5% to about 10%, about 2.5% to about 12.5%, about 2.5% to about 15%, about 2.5% to about 17.5%, about 2.5% to about 20%, about 2.5% to about 22.5%, about 2.5% to about 25%, about 5% to about 7.5%, about 5% to about 10%, about 5% to about 12.5%, about 5% to about 15%, about 5% to about 17.5%, about 5% to about 20%, about 5% to about 22.5%, about 5% to about 25%, about 7.5% to about 10%, about 7.5% to about 12.5%, about 7.5% to about 15%, about 7.5% to about 17.5%, about 7.5% to about 20%, about 7.5% to about 22.5%, about 7.5% to about 25%, about 10% to about 12.5%, about 10% to about 15%, about 10% to about 17.5%, about 10% to about 20%, about 10% to about 22.5%, about 10% to about 25%, about 12.5% to about 15%, about 12.5% to about 17.5%, about 12.5% to about 20%, about 12.5% to about 22.5%, about 12.5% to about 25%, about 15% to about 17.5%, about 15% to about 20%, about 15% to about 22.5%, about 15% to about 25%, about 17.5% to about 20%, about 17.5% to about 22.5%, about 17.5% to about 25%, about 20% to about 22.5%, about 20% to about 25%, or about 222.5% to about 25% of the total weight of the polymer matric material.

A therapeutic agent can comprise a drug may be any of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and prostaglandin analogues, and hypotensive lipids, and combinations thereof, antimicrobial agent (e.g., antibiotic, antiviral, antiparacytic, antifungal, etc.), a corticosteroid or other anti-inflammatory (e.g., a NSAID), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre- and post-surgical treatments, dry eye, inflammation of the nasal lacrimal duct system, and allergies including allergic rhinitis.

In various embodiments, the therapeutic agent is an ophthalmic drug including, but not limited to bimatoprost, travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluorometholone or a combination thereof. In various embodiments, the ophthalmic drug is latanoprost.

In various embodiments, the therapeutic agent includes cyclosporine, steroid, loteprednol, fluoromethalone, non-penetrating steroid, free acid of steroid, non-steroidal anti-inflammatory, ketorolac, small-molecule integrin antagonist, lifitegrast, doxycycline, azithromycin, lipid, fatty alcohol, cetyl alcohol, stearyl alcohol, fatty acid, long chain fatty acid, oil, and silicone oil. In various embodiments, the therapeutic agent is a steroid.

A drug depot disclosed herein comprises is composed of a matrix polymer and coating layer. Materials used to make a polymer matrix and coating layer disclosed herein are biocompatible materials. Biocompatible materials disclosed herein are non-immunogenic and substantially inert with respect to body tissues that a self-retaining implantable drug delivery device disclosed herein come into contact with. Suitable biocompatible materials include, but are not limited to, polyurethanes, hydrocarbon polymers, polyacrylic esters, silicone polymers, and the like.

A polymer matrix disclosed herein forms a dispersion with the one or more therapeutic agents upon curing. In one embodiment, polymer matrix disclosed herein forms a solid dispersion with the one or more therapeutic agents. In another embodiment, a polymer matrix disclosed herein forms a liquid dispersion with the one or more therapeutic agents.

A polymer matrix disclosed herein is preferable a silicone polymer matrix. Silicones or polysiloxanes are widely used in biomedical applications but there are a relatively small number of manufacturers that have the required purity for the healthcare market. Silicone chemistry is well-known and is described in the classic text of Walter Noll "Chemistry and Technology of Silicones, Academic Press, New York, 1968. Another useful text is by Wilfred Lynch "Handbook of Silicone Rubber Fabrication, Van Nostrand Reinhold Company, New York, 1978. The chemistries in this text are included in this application. Silicones also have a long history for drug delivery applications because of their adaptability to include a number of drugs, ease of formulation and mild curing conditions. Two common curing conditions use platinum or tin catalysis. Silicones containing vinyl groups and Si—H bonds are readily crosslinked under platinum catalysis by an addition reaction; while, alkoxy and hydroxyl containing polymers can cure by a condensation reaction under tin catalysis. There are a number of other curing systems which can be used and these are well known to a person of skill in the art.

A drug depot disclosed herein comprises one or more coating layers that coat the outer surface of a drug depot. The one or more coating layers help control the release of the one or more therapeutic agents contained in the drug depot in a manner desired. Suitable coatings can include polymers or metals. Polymer coatings are organic materials typically applied by dip-coating, spray-coating-spin-coating, layer-by-layer, self-assembled monolayers, chemical vapor deposition and so on. There are a number of manufactures of coatings, e.g., poly(p-xylylene) polymer including parylenes, such as, e.g., Parylene C and Parylene N, Lubrizol which sells TECOFLEX™, TECOPHILIC™ and SANCURE™ coatings which have been used in the ocular device literature, see, e.g., US2010/0048758, incorporated by reference herein in its entirety. Metallic coating can be applied for example by vapor deposition techniques such as sputtering. Such metallic coatings include platinum and titanium.

In aspects of this embodiment, a drug depot disclosed herein comprises, e.g., one, two, three, four, or five coating layers. In one aspect, a drug depot disclosed herein comprises one, two, three four or five coating layers. In other aspects of this embodiment, a drug depot disclosed herein comprises, e.g., at least one, at least two, at least three, at least four or at least five coating layers. In yet other aspects of this embodiment, a drug depot disclosed herein comprises, e.g., at most one, at most two, at most three, at most four or at most five coating layers. In yet other aspects of this embodiment, a drug depot disclosed herein comprises, e.g., 1 to 2 coating layers, 1 to 3 coating layers, 1 to 4 coating layers, 1 to 5 coating layers, 2 to 3 coating layers, 2 to 4 coating layers, 2 to 5 coating layers, 3 to 4 coating layers, 3 to 5 coating layers, or 3 to 5 coating layers. A drug depot disclosed herein comprises two or more coating layers can have each layer being comprises of a polymer, each layer being comprised of a metal, or the two or more layers being a combination of polymer coating layers and metal coating layers. In one embodiment, a drug depot disclosed herein comprises a polymer coating layer next to the polymer matrix and a metal coating layer over the polymer coating layer.

It is preferable that a coating layer a drug depot be thin to ensure good adhesion and integrity. In one embodiment, a polymer layer coating the surface of a drug depot will be, e.g., about 0.001 μm to about 100 μm in thickness. In aspects of this embodiment, a coating layer of a drug depot will be, e.g., about 0.1 μm, about 0.2 μm, about 0.3 μm, about 0.4 μm, about 0.5 μm, about 0.6 μm, about 0.7 μm, about 0.8 μm, about 0.9 μm, about 1.0 μm, about 1.5 μm, about 2.0 μm, about 2.5 μm, about 3.0 μm, about 3.5 μm, about 4.0 μm, about 4.5 μm, or about 5.0 μm. In other aspects of this embodiment, a coating layer of a drug depot will be, e.g., at least 0.1 μm, at least 0.2 μm, at least 0.3 μm, at least 0.4 μm, at least 0.5 μm, at least 0.6 μm, at least 0.7 μm, at least 0.8 μm, at least 0.9 μm, at least 1.0 μm, at least 1.5 μm, at least 2.0 μm, at least 2.5 μm, at least 3.0 μm, at least 3.5 μm, at least 4.0 μm, at least 4.5 μm, or at least 5.0 μm. In other aspects of this embodiment, a coating layer of a drug depot will be, e.g., at most 0.1 µm, at most 0.2 µm, at most 0.3 µm, at most 0.4 µm, at most 0.5 µm, at most 0.6 µm, at most 0.7 µm, at most 0.8 µm, at most 0.9 µm, at most 1.0 µm, at most 1.5 µm, at most 2.0 µm, at most 2.5 µm, at most 3.0 µm, at most 3.5 µm, at most 4.0 µm, at most 4.5 µm, or at most 5.0 µm.

In still other aspects of this embodiment, a coating layer of a drug depot will be, e.g., about 0.1 µm to about 0.2 µm, about 0.1 µm to about 0.3 µm, about 0.1 µm to about 0.4 µm, about 0.1 µm to about 0.5 µm, about 0.1 µm to about 0.6 µm, about 0.1 µm to about 0.7 µm, about 0.1 µm to about 0.8 µm, about 0.1 µm to about 0.9 µm, about 0.1 µm to about 1.0 µm, about 0.1 µm to about 2.0 µm, about 0.1 µm to about 3.0 µm, about 0.1 µm to about 4.0 µm, about 0.1 µm to about 5.0 µm, about 0.2 µm to about 0.3 µm, about 0.2 µm to about 0.4 µm, about 0.2 µm to about 0.5 µm, about 0.2 µm to about 0.6 µm, about 0.2 µm to about 0.7 µm, about 0.2 µm to about 0.8 µm, about 0.2 µm to about 0.9 µm, about 0.2 µm to about 1.0 µm, about 0.2 µm to about 2.0 µm, about 0.2 µm to about 3.0 µm, about 0.2 µm to about 4.0 µm, about 0.3 µm to about 5.0 µm, about 0.3 µm to about 0.4 µm, about 0.3 µm to about 0.5 µm, about 0.3 µm to about 0.6 µm, about 0.3 µm to about 0.7 µm, about 0.3 µm to about 0.8 µm, about 0.3 µm to about 0.9 µm, about 0.3 µm to about 1.0 µm, about 0.3 µm to about 2.0 µm, about 0.3 µm to about 3.0 µm, about 0.3 µm to about 4.0 µm, about 0.3 µm to about 5.0 µm, about 0.4 µm to about 0.5 µm, about 0.4 µm to about 0.6 µm, about 0.4 µm to about 0.7 µm, about 0.4 µm to about 0.8 µm, about 0.4 µm to about 0.9 µm, about 0.4 µm to about 1.0 µm, about 0.4 µm to about 2.0 µm, about 0.4 µm to about 3.0 µm, about 0.4 µm to about 4.0 µm, about 0.4 µm to about 5.0 µm, about 0.5 µm to about 0.6 µm, about 0.5 µm to about 0.7 µm, about 0.5 µm to about 0.8 µm, about 0.5 µm to about 0.9 µm, about 0.5 µm to about 1.0 µm, about 0.5 µm to about 2.0 µm, about 0.5 µm to about 3.0 µm, about 0.5 µm to about 4.0 µm, about 0.5 µm to about 5.0 µm, about 0.6 µm to about 0.7 µm, about 0.6 µm to about 0.8 µm, about 0.6 µm to about 0.9 µm, about 0.6 µm to about 1.0 µm, about 0.6 µm to about 2.0 µm, about 0.6 µm to about 3.0 µm, about 0.6 µm to about 4.0 µm, about 0.6 µm to about 5.0 µm, about 0.7 µm to about 0.8 µm, about 0.7 µm to about 0.9 µm, about 0.7 µm to about 1.0 µm, about 0.7 µm to about 2.0 µm, about 0.7 µm to about 3.0 µm, about 0.7 µm to about 4.0 µm, about 0.7 µm to about 5.0 µm, about 0.8 µm to about 0.9 µm, about 0.8 µm to about 1.0 µm, about 0.8 µm to about 2.0 µm, about 0.8 µm to about 3.0 µm, about 0.8 µm to about 4.0 µm, about 0.8 µm to about 5.0 µm, about 0.9 µm to about 1.0 µm, about 0.9 µm to about 2.0 µm, about 0.9 µm to about 3.0 µm, about 0.9 µm to about 4.0 µm, about 0.9 µm to about 5.0 µm, about 1.0 µm to about 2.0 µm, about 1.0 µm to about 3.0 µm, about 1.0 µm to about 4.0 µm, or about 1.0 µm to about 5.0 µm, in thickness.

In aspects of this embodiment, a coating layer of a drug depot will be, e.g., about 5 µm, about 10 µm, about 20 µm, about 30 µm, about 40 µm, about 50 µm, about 60 µm, about 70 µm, about 80 µm, about 90 µm, or about 100 µm in thickness. In other aspects of this embodiment, a coating layer of a drug depot will be, e.g., at least 5 µm, at least 10 µm, at least 20 µm, at least 30 µm, at least 40 µm, at least 50 µm, at least 60 µm, at least 70 µm, at least 80 µm, at least 90 µm, or at least 100 µm in thickness. In yet other aspects of this embodiment, a coating layer of a drug depot will be, e.g., at most 5 µm, at most 10 µm, at most 20 µm, at most 30 µm, at most 40 µm, at most 50 µm, at most 60 µm, at most 70 µm, at most 80 µm, at most 90 µm, or at most 100 µm in thickness. In yet other aspects of this embodiment, a coating layer of a drug depot will be, e.g., about 5 µm to 10 µm, about 5 µm to 20 µm, about 5 µm to 30 µm, about 5 µm to 40 µm, about 5 µm to 50 µm, about 5 µm to 60 µm, about 5 µm to 70 µm, about 5 µm to 80 µm, about 5 µm to 90 µm, about 5 µm to 100 µm, about 10 µm to 20 µm, about 10 µm to 30 µm, about 10 µm to 40 µm, about 10 µm to 50 µm, about 10 µm to 60 µm, about 10 µm to 70 µm, about 10 µm to 80 µm, about 10 µm to 90 µm, about 10 µm to 100 µm, about 20 µm to 30 µm, about 20 µm to 40 µm, about 20 µm to 50 µm, about 20 µm to 60 µm, about 20 µm to 70 µm, about 20 µm to 80 µm, about 20 µm to 90 µm, about 20 µm to 100 µm, about 30 µm to 40 µm, about 30 µm to 50 µm, about 30 µm to 60 µm, about 30 µm to 70 µm, about 30 µm to 80 µm, about 30 µm to 90 µm, about 30 µm to 100 µm, about 40 µm to 50 µm, about 40 µm to 60 µm, about 40 µm to 70 µm, about 40 µm to 80 µm, about 40 µm to 90 µm, about 40 µm to 100 µm, about 50 µm to 60 µm, about 50 µm to 70 µm, about 50 µm to 80 µm, about 50 µm to 90 µm, about 50 µm to 100 µm, about 60 µm to 70 µm, about 60 µm to 80 µm, about 60 µm to 90 µm, about 60 µm to 100 µm, about 70 µm to 80 µm, about 70 µm to 90 µm, about 70 µm to 100 µm, about 80 µm to 90 µm, about 80 µm to 100 µm, or about 90 µm to 100 µm in thickness.

The surface of a polymer matrix disclosed herein may need a primer and/or an adhesion promoter applied to ensure good adhesion of the one or more coating polymers to the surface of the drug depot. For example, adhesion of the coating layer to the polymer matrix in an aqueous environment could result in loss of adhesion and the separation of the coating layer from the polymer matrix. Silicone adhesives and MED-160 primer and various NUSIL® adhesives are described in U.S. Pat. No. 9,781,842, which is hereby incorporated by reference in its entirety. In other aspects, the surface of the drug depot can undergo plasma treatment to enhance surface hydrophilicity.

In one embodiment, a drug depot has a layer of one or more impermeable polymers coated over its surface to create an impermeable membrane. Controlled release of one or more therapeutic agents is achieved by creating a small region or regions that are uncoated to provide an opening for drug release. This can be achieved by for example masking small region(s) of a polymer matrix and then coating with a polymer or metal to form a coating layer. Alternatively, a polymer matric can first be completely coated with a polymer or metal and then puncturing the coating layer to form openings. Such puncturing can be achieved using a mechanical mechanism such as needle piercing or by laser etching or drilling. Such procedures are described in Hans Griesser "Thin Film Coatings for Biomaterials and Biomedical Applications, Elsevier, Cambridge, 2016" which is hereby incorporated by reference in its entirety.

Openings of the coating layer can be surface pores or depot channels. A surface pore is an opening only through the coating layer but leaves the polymer matrix intact. A depot channel is a tunnel through the entire drug depot (i.e., coating layer and polymer matrix) from one end to the other end. In aspects of this embodiment, a drug depot disclosed herein has one, two, three, four or five surface pores. In other aspects of this embodiment, a drug depot disclosed herein has at least one, at least two, at least three, at least four or at least five surface pores. In yet other aspects of this embodiment, a drug depot disclosed herein has at most one, at most two, at most three, at most four or at most five surface pores. In still other aspects of this embodiment, a drug depot disclosed herein has, e.g., about 1 to about 2 surface pores, about 1 to about 3 surface pores, about 1 to about 4 surface pores, about 1 to about 5 surface pores, about 2 to about 3 surface pores, about 2 to about 4 surface pores, about 2 to about 5 surface pores, about 3 to about 4 surface pores, about 3 to about 5 surface pores, or about 4 to about 5 surface pores.

In aspects of this embodiment, a drug depot disclosed herein has one, two, three, four or five depot channels. In other aspects of this embodiment, a drug depot disclosed herein has at least one, at least two, at least three, at least four or at least five depot channels. In yet other aspects of this embodiment, a drug depot disclosed herein has at most one, at most two, at most three, at most four or at most five depot channels. In still other aspects of this embodiment, a drug depot disclosed herein has, e.g., about 1 to about 2 depot channels, about 1 to about 3 depot channels, about 1 to about 4 depot channels, about 1 to about 5 depot channels, about 2 to about 3 depot channels, about 2 to about 4 depot channels, about 2 to about 5 depot channels, about 3 to about 4 depot channels, about 3 to about 5 depot channels, or about 4 to about 5 depot channels.

In various embodiments, the one or more therapeutic agents will be released simultaneously with each depot having its own release rate. In various embodiments, the one or more therapeutics will be released sequentially with each depot having its own release rate.

A drug depot disclosed herein may be formulated in a controlled release delivery platform including a sustained release formulation and an extended release formulation. The ocular surface is a tough target tissue to administer a drug to as tear production immediately dilutes any active ingredient. Further, blinking provides another source of immediate dilution and removal of any active ingredient being delivered. The use of a controlled release delivery platform adheres of the ocular surface to ensure that one or more therapeutics contained in a drug depot disclosed herein remains for a time sufficient to deliver the required dose necessary for therapeutic effect. Such controlled release delivery platform can improve the delivery kinetics of one or more therapeutics disclosed herein by releasing in a time-controlled fashion, potentially minimizing the number of instillations required over a course of treatment.

An extended release formulation refers to the release of one or more therapeutics disclosed herein over a period of time of less than about seven days. A sustained release formulation refers to the release of one or more therapeutics disclosed herein over a period of about seven days or more.

In aspects of this embodiment, as a sustained release formulation a drug depot disclosed herein releases one or more therapeutics disclosed herein with approximate zero order release kinetics over a period of, e.g., about 7 days, about 15 days after administration, about 30 days, about 45 days, about 60 days, about 75 days, or about 90 days after administration. In other aspects of this embodiment, as a sustained release formulation a drug depot disclosed herein releases one or more therapeutics disclosed herein with approximate zero order release kinetics over a period of, e.g., at least 7 days, at least 15 days, at least 30 days, at least 45 days, at least 60 days, at least 75 days, or at least 90 days after administration. In yet other aspects of this embodiment, a drug depot disclosed herein releases one or more therapeutics disclosed herein with approximate first order release kinetics over a period of, e.g., about 7 days to about 30 days, about 7 days to about 45 days, about 7 days to about 60 days, about 7 days to about 75 days, about 7 days to about 90 days, about 15 days to about 30 days, about 15 days to about 45 days, about 15 days to about 60 days, about 15 days to about 75 days, about 15 days to about 90 days, about 30 days to about 45 days, about 30 days to about 60 days, about 30 days to about 75 days, about 30 days to about 90 days, about 45 days to about 60 days, about 45 days to about 75 days, about 45 days to about 90 days, about 60 days to about 75 days, about 60 days to about 90 days, about 75 days to about 90 days after administration. In other aspects of this embodiment, as a sustained release formulation a drug depot disclosed herein releases one or more therapeutics disclosed herein with approximate first order release kinetics over a period of, e.g., about 7 days, about 15 days after administration, about 30 days, about 45 days, about 60 days, about 75 days, or about 90 days after administration. In yet other aspects of this embodiment, a drug depot disclosed herein releases one or more therapeutics disclosed herein with approximate first order release kinetics over a period of, e.g., at least 7 days, at least 15 days, at least 30 days, at least 45 days, at least 60 days, at least 75 days, or at least 90 days after administration. In still other aspects of this embodiment, a drug depot disclosed herein releases one or more therapeutics disclosed herein with approximate first order release kinetics over a period of, e.g., about 7 days to about 30 days, about 7 days to about 45 days, about 7 days to about 60 days, about 7 days to about 75 days, about 7 days to about 90 days, about 15 days to about 30 days, about 15 days to about 45 days, about 15 days to about 60 days, about 15 days to about 75 days, about 15 days to about 90 days, about 30 days to about 45 days, about 30 days to about 60 days, about 30 days to about 75 days, about 30 days to about 90 days, about 45 days to about 60 days, about 45 days to about 75 days, about 45 days to about 90 days, about 60 days to about 75 days, about 60 days to about 90 days, about 75 days to about 90 days after administration.

In aspects of this embodiment, as a sustained release formulation a drug depot disclosed herein releases one or more therapeutics disclosed herein with approximate zero order release kinetics over a period of, e.g., about 3 months, about 4 months, about 5 months, about 6 months, about 7 months, about 8 months, about 9 months, about 10 months, about 11 months or about 12 months after administration. In other aspects of this embodiment, as a sustained release formulation a drug depot disclosed herein releases one or more therapeutics disclosed herein with approximate zero order release kinetics over a period of, e.g., at least 3 months, at least 4 months, at least 5 months, at least 6 months, at least 7 months, at least 8 months, at least 9 months, at least 10 months, at least 11 months or at least 12 months after administration after administration. In yet other aspects of this embodiment, a drug depot disclosed herein releases one or more therapeutics disclosed herein with approximate zero order release kinetics over a period of, e.g., about 3 months to about 6 months, about 3 months to about 9 months, about 3 months to about 12 months, about 6 months to about 9 months, about 6 months to about 12 months, or about 6 months to about 12 months after administration. In other aspects of this embodiment, as a sustained release formulation a drug depot disclosed herein releases one or more therapeutics disclosed herein with approximate first order release kinetics over a period of, e.g., about 3 months, about 4 months, about 5 months, about 6 months, about 7 months, about 8 months, about 9 months, about 10 months, about 11 months or about 12 months after administration after administration. In yet other aspects of this embodiment, a drug depot disclosed herein releases one or more therapeutics disclosed herein with approximate first order release kinetics over a period of, e.g., at least 3 months, at least 4 months, at least 5 months, at least 6 months, at least 7 months, at least 8 months, at least 9 months, at least 10 months, at least 11 months or at least 12 months after administration. In still other aspects of this embodiment, a drug depot disclosed herein releases one or more therapeutics disclosed herein with approximate first order release kinetics over a period of, e.g., about 3 months to about 6 months, about 3 months to about 9 months, about 3 months to about 12 months, about 6 months to about 9 months, about 6 months to about 12 months, or about 6 months to about 12 months after administration.

In aspects of this embodiment, as a sustained release formulation a drug depot disclosed herein releases one or more therapeutics disclosed herein with approximate zero order release kinetics over a period of, e.g., about 1 year, about 2 years, about 3 years, about 4 years, or about 5 years after administration. In other aspects of this embodiment, as a sustained release formulation a drug depot disclosed herein releases one or more therapeutics disclosed herein with approximate zero order release kinetics over a period of, e.g., at least 1 year, at least 2 years, at least 3 years, at least 4 years, or at least 5 years after administration after administration. In yet other aspects of this embodiment, as a sustained release formulation a drug depot disclosed herein releases one or more therapeutics disclosed herein with approximate zero order release kinetics over a period of, e.g., about 1 year to about 2 years, about 1 year to about 3 years, about 1 year to about 4 years, about 1 year to about 5 years, about 2 years to about 3 years, about 2 years to about 4 years, about 2 years to about 5 years, about 3 years to about 4 years, about 3 years to about 5 years, or about 4 years to about 5 years after administration after administration. In other aspects of this embodiment, as a sustained release formulation a drug depot disclosed herein releases one or more therapeutics disclosed herein with approximate first order release kinetics over a period of, e.g., about 1 year, about 2 years, about 3 years, about 4 years, or about 5 years after administration after administration. In yet other aspects of this embodiment, a drug depot disclosed herein releases one or more therapeutics disclosed herein with approximate first order release kinetics over a period of, e.g., at least 1 year, at least 2 years, at least 3 years, at least 4 years, or at least 5 years after administration. In still other aspects of this embodiment, as a sustained release formulation a drug depot disclosed herein releases one or more therapeutics disclosed herein with approximate first order release kinetics over a period of, e.g., about 1 year to about 2 years, about 1 year to about 3 years, about 1 year to about 4 years, about 1 year to about 5 years, about 2 years to about 3 years, about 2 years to about 4 years, about 2 years to about 5 years, about 3 years to about 4 years, about 3 years to about 5 years, or about 4 years to about 5 years after administration after administration.

In aspects of this embodiment, as an extended release formulation a drug depot disclosed herein releases one or more therapeutics disclosed herein with approximate zero order release kinetics over a period of, e.g., about 1 day, about 2 days, about 3 days, about 4 days, about 5 days, about 6 days, or about 7 days after administration. In other aspects of this embodiment, as an extended release formulation a drug depot disclosed herein releases one or more therapeutics disclosed herein with approximate zero order release kinetics over a period of, e.g., at most 1 day, at most 2 days, at most 3 days, at most 4 days, at most 5 days, at most 6 days, or at most 7 days after administration. In yet other aspects of this embodiment, as an extended release formulation a drug depot disclosed herein releases one or more therapeutics disclosed herein with approximate first order release kinetics over a period of, e.g., about 1 day, about 2 days, about 3 days, about 4 days, about 5 days, about 6 days, or about 7 days after administration. In still other aspects of this embodiment, as an extended release formulation a drug depot disclosed herein releases one or more therapeutics disclosed herein with approximate first order release kinetics over a period of, e.g., at most 1 day, at most 2 days, at most 3 days, at most 4 days, at most 5 days, at most 6 days, or at most 7 days after administration.

A self-retaining implantable drug delivery device disclosed herein can be adapted to provide delivery of drug at a daily rate that is substantially below the therapeutically effective drop form of treatment so as to provide a large therapeutic range with a wide safety margin. For example, many embodiments treat the eye with therapeutic levels for extended periods that are no more than 5% or 10% of the daily drop dosage. Consequently, during an initial bolus or washout period of about one to three days, the implant can elute the therapeutic agent at a rate that is substantially higher than the sustained release levels and well below the daily drop form dosage. For example, with an average sustained release level of 100 ng per day, and an initial release rate of 1000 ng to 1500 ng per day, the amount of drug initially released is less than the 2500 ng of drug that may be present in a drop of drug delivered to the eye. This used use of sustained release levels substantially below the amount of drug in a drop and/or drops administered daily allows the device to release a therapeutically beneficial amount of drug to achieve the desired therapeutic benefit with a wide safety margin, while avoiding an inadequate or excessive amount of drug at the intended site or region. An extended period of time may mean a relatively short period of time, for example minutes or hours (such as with the use of an anesthetic), through days or weeks (such as the use of pre-surgical or post-surgical antibiotics, steroids, or NSAIDs and the like), or longer (such as in the case of glaucoma treatments), for example months or years (on a recurring basis of use of the device).

In aspects of this embodiment, a self-retaining implantable drug delivery device disclosed herein releases a therapeutic agent in a range of 10 ng/day to about 5 μg/day. In aspects of this embodiment, a self-retaining implantable drug delivery device disclosed herein has a release rate of, e.g., about 10 ng/day, about 25 ng/day, about 50 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 μg/day, about 2 μg/day, about 3 μg/day, about 4 μg/day, or about 5 μg/day. In other aspects of this embodiment, a self-retaining implantable drug delivery device disclosed herein has a release rate of, e.g., at least 10 ng/day, at least 25 ng/day, at least 50 ng/day, at least 100 ng/day, at least 200 ng/day, at least 300 ng/day, at least 400 ng/day, at least 500 ng/day, at least 600 ng/day, at least 700 ng/day, at least 800 ng/day, at least 900 ng/day, at least 1 μg/day, at least 2 μg/day, at least 3 μg/day, at least 4 μg/day, or at least 5 μg/day. In yet other aspects of this embodiment, a self-retaining implantable drug delivery device disclosed herein has a release rate of, e.g., at most 10 ng/day, at most 25 ng/day, at most 50 ng/day, at most 100 ng/day, at most 200 ng/day, at most 300 ng/day, at most 400 ng/day, at most 500 ng/day, at most 600 ng/day, at most 700 ng/day, at most 800 ng/day, at most 900 ng/day, at most 1 μg/day, at most 2 μg/day, at most 3 μg/day, at most 4 μg/day, or at most 5 μg/day. In yet other aspects of this embodiment, a self-retaining implantable drug delivery device disclosed herein has a release rate of, e.g., about 10 ng/day to about 50 ng/day, about 10 ng/day to about 100 ng/day, about 10 ng/day to about 250 ng/day, about 10 ng/day to about 500 ng/day, about 50 ng/day to about 100 ng/day, about 50 ng/day to about 250 ng/day, about 50 ng/day to about 500 ng/day, about 50 ng/day to about 750 ng/day, about 50 ng/day to about 1 µg/day, about 100 ng/day to about 250 ng/day, about 100 ng/day to about 500 ng/day, about 100 ng/day to about 750 ng/day, about 100 ng/day to about 1,000 ng/day, about 500 ng/day to about 750 ng/day, about 500 ng/day to about 1 µg/day, about 500 ng/day to about 2 µg/day, about 500 ng/day to about 3 µg/day, about 500 ng/day to about 4 µg/day, about 500 ng/day to about 5 µg/day, about 750 ng/day to about 1 µg/day, about 750 ng/day to about 2 µg/day, about 750 ng/day to about 3 µg/day, about 750 ng/day to about 4 µg/day, about 750 ng/day to about 5 µg/day, about 1 µg/day to about 2 µg/day, about 1 µg/day to about 3 µg/day, about 1 µg/day to about 4 µg/day, or about 1 µg/day to about 5 µg/day.

A self-retaining implantable drug delivery device disclosed herein may further comprise a biosensor capable of detecting and monitoring physical, biochemical and/or physiological properties of an individual. A biosensor can be placed in any location in a self-retaining implantable drug delivery device disclosed herein as long as the biosensor is capable of sensing or detecting the physical, biochemical and/or physiological properties it is-indented intended to monitor. A biosensor disclosed herein may include a passive or active radio frequency emitter, or a miniature sonic resonator, and the like which can be coupled with a miniature microprocessor mounted in a self-retaining implantable drug delivery device disclosed herein. A biosensor mounted in a self-retaining implantable drug delivery device disclosed herein can be remotely driven by ultrasonic waves, infra-red radiation, or alternatively remotely powered by electromagnetic waves or by incident light. A biosensor can also be powered by microminiature low voltage batteries which are incorporated into the body of a biosensor or self-retaining implantable drug delivery device disclosed herein.

In an aspect of this embodiment, a canalicular stent disclosed herein may further comprise a biosensor capable of detecting and monitoring a bodily fluid from the eye (e.g., tear fluid) and/or intraocular pressure (IOP). Such a biosensor is positioned in the body of the canalicular stent so as to be exposed to contact with tear fluid making contact with the outer surface of the stent. For example, a biosensor can be positioned centrally within an elongated body so as to be immediately adjacent or protruding from a punctum when a canalicular stent is in place in the canaliculus of a human eyelid.

Many biosensors for measuring intraocular pressure are known and several may be adapted to produce an IOP-measuring biosensor that can be incorporated into a canalicular stent disclosed herein, see, e.g., TRIGGERFISH® continuous ocular dimensional change monitoring system (Sensimed AG. Lausanne CH) which provides a contact lens-type monitoring system that captures spontaneous circumferential changes at the corneoscleral area and transmits data to a portable recorder device worn by the patient. Other IOP measuring technologies that may be-adapted to in situ pressure measurement by incorporation into a stent of this invention include but are not limited to Goldmann applanation tonometry, PASCAL® Dynamic Contour Tonometer (Ziemer Ophthalmic Systems AG, Port CH), TONO-PEN® (Reichert Ophthalmic Instruments Inc., Depew NY, US), MODEL 30™ pneumatonometer (Reichert Ophthalmic Instruments Inc.). See, Eisenberg, D., "Reconsidering the Gold Standard of Tonometry," Glaucoma Today, Early Spring 2011. See, also, U.S. Pat. No. 7,403,805, incorporated herein by reference. The biosensor canaliculus stent having tonometric capabilities provides distinct, advantages over extraocular and contact lens-type instruments in that it can provide constant or continuous readouts of IOP and avoids irritation of the cornea, as can occur with standard tonometric devices. The IOP stent can also provide pressure data away from the physician's office, without the use of anesthetic eye drops. The patient can take a pressure reading at any time by pressing the device against the sclera or by simply looking toward their nose, depending on the type of IOP sensor. As with the tear film sensors, signals from the sensor may be recorded for later download in a resident microchip or transmitted via an antenna to a device such as a smartphone, computer, or other monitor, e.g., wearable activity monitors (such as FITBIT® wristband analyzers).

In one embodiment, the present specification discloses a self-retaining bicanalicular device comprising a tubing which forms a semi-rigid cylindrical tube having a first distal end, a second distal end, an elongated body between the first distal end and the second distal end, and one or more drug depots including one or more therapeutic agents. The tubing can have an outer diameter of about 0.5 mm to about 0.7 mm, an inner diameter of about 0.2 mm to about 0.4 mm and a length of about 20 mm to about 30 mm. The one or more drug depots are centrally located with respect to the elongated body. Preferably, after placement in the canaliculi, the centrally located one or more drug depots would be positioned at the medial canthus. One or more winglets are present at either the first distal end or the second distal end.

In one embodiment, the present specification discloses a self-retaining bicanalicular device comprising a tubing which forms a semi-rigid cylindrical tube having a first distal end, a second distal end, an elongated body between the first distal end and the second distal end, and one or more drug depots including one or more therapeutic agents. The tubing can have an outer diameter of about 0.5 mm to about 0.7 mm, an inner diameter of about 0.2 mm to about 0.4 mm and a length of about 20 mm to about 30 mm. The one or more drug depots are centrally located with respect to the elongated body. Preferably, after placement in the canaliculi, the centrally located one or more drug depots would be positioned at the medial canthus. One or more winglets are present at both the first and second distal ends.

In one embodiment, the present specification discloses a self-retaining unicanalicular device comprising a tubing which forms a semi-rigid cylindrical tube having a first distal end, a second distal end, an elongated body between the first distal end and the second distal end, and one or more drug depots including one or more therapeutic agents. The tubing can have an outer diameter of about 0.5 mm to about 0.7 mm, an inner diameter of about 0.2 mm to about 0.4 mm and a length of about 10 mm to about 15 mm. The one or more drug depots are located at either the first distal end or the second distal end.

In one embodiment, the present specification discloses a self-retaining unicanalicular device comprising a tubing which forms a semi-rigid cylindrical tube having a first distal end, a second distal end, an elongated body between the first distal end and the second distal end, and one or more drug depots including one or more therapeutic agents. The tubing can have an outer diameter of about 0.5 mm to about 0.7 mm, an inner diameter of about 0.2 mm to about 0.4 mm and a length of about 10 mm to about 15 mm. The one or more drug depots are located at the first distal end while one or more winglets are present at the second distal end. Alternatively, the one or more drug depots are located at the second distal end while one or more winglets are present at the first distal end.

Figure 2A:
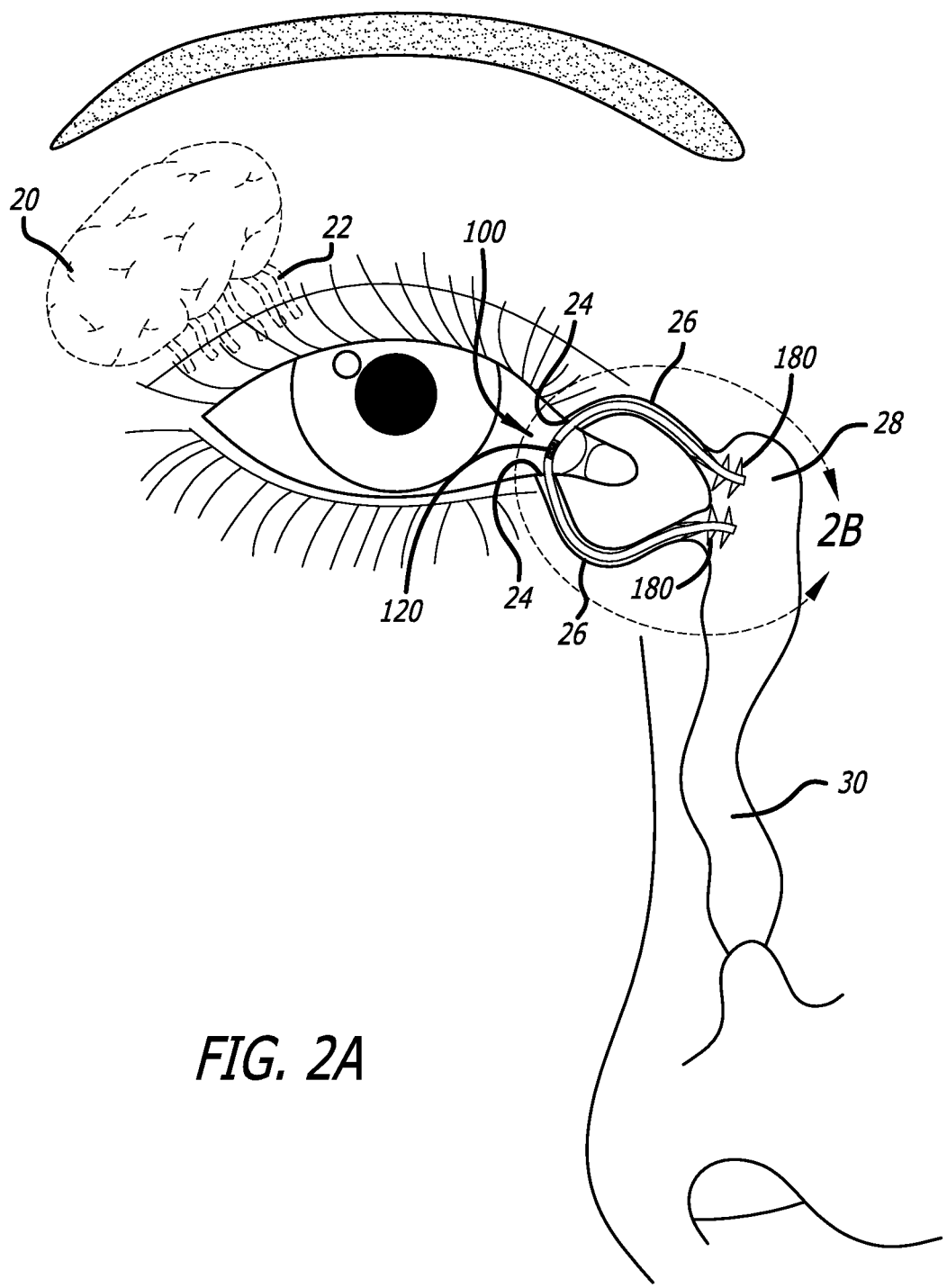
FIGS. 2A-F shows placement of a self-retaining implantable drug delivery device disclosed herein in the lacrimal drainage system of the eye with FIGS. 2A-B showing placement of a bicanalicular stent using anchors comprising flexible winglets.
Figure 2B:
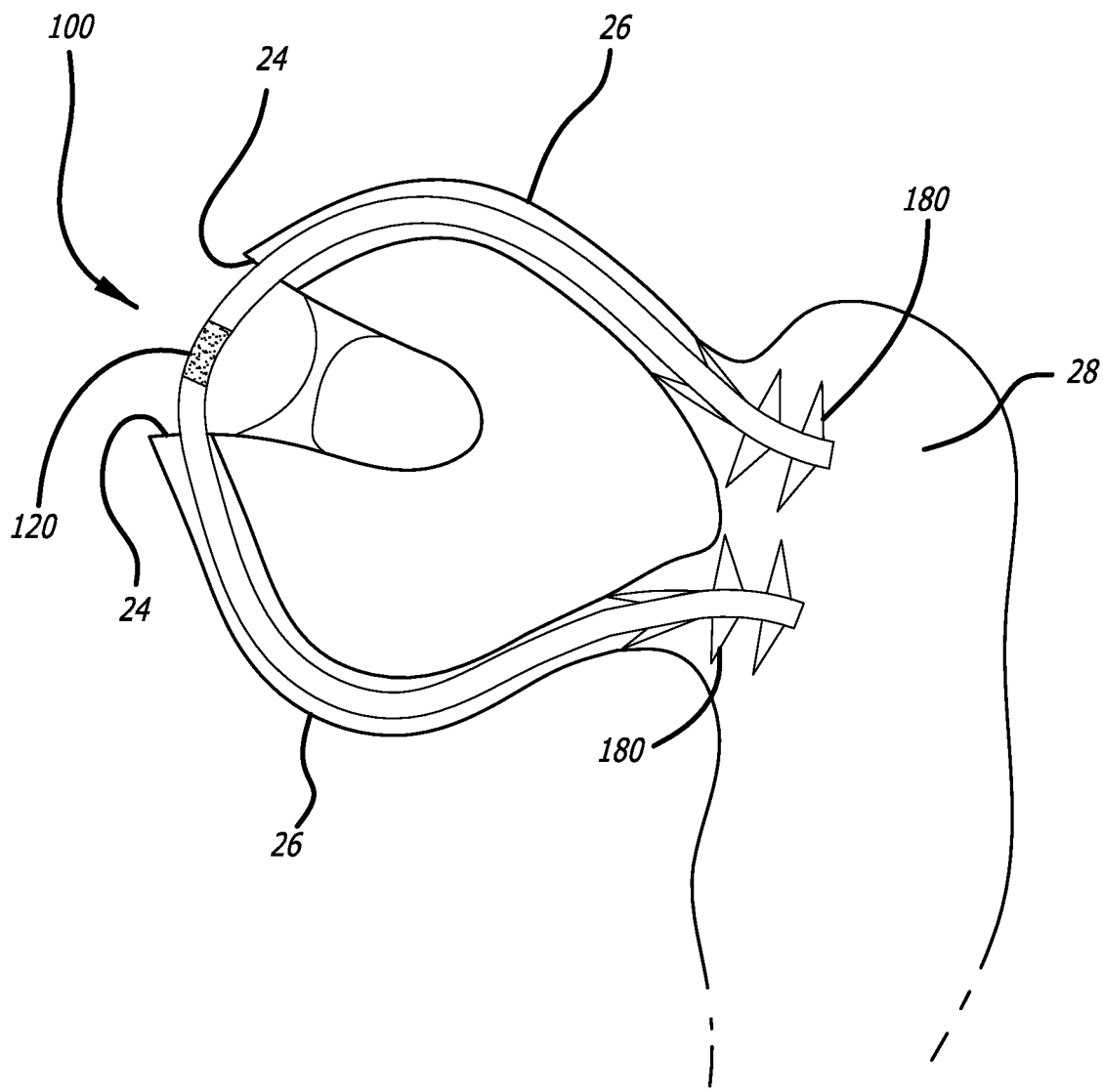

Referring to FIGS. 2A-B and using a method of treating glaucoma as an example, a patient will be placed at slit lamp after applying topical anesthetic eye drops (tetracaine) in each eye. A standard punctal dilator will then be manipulated by physician to dilate punctum to about 0.8 mm. This will be done to both the superior and inferior punctum 24. A small amount of lubricant, such as, e.g., CELLUVISC®, can be applied to tip of a bicanalicular stent 100 adjacent to winglets 180 to facilitate introduction of device. Either using small forceps holding distal end of tube (about 3.0 mm to about 4.0 mm from end perpendicular to bicanalicular stent 100 either end (superior or inferior), the distal end of bicanalicular stent 100 can be advanced into punctum 24 then ampulla and then forward into a canaliculus 26. This can be similarity done with the metal stylet which should also provide a firm stop when touching opposite side of lacrimal sac 28. In any case the self-retaining winglets 180 will then spring open once entering lacrimal sac cavity 28. Gentle counter traction can then take place with forceps to ensure proper fixation of bicanalicular stent 100 in lacrimal sac 28. The same procedure is then carried out with the other end of bicanalicular stent 100 through the other punctum, ampulla, and canaliculus. Although FIG. 2A-B show positioning of a bicanalicular stent 100 in the inferior and superior canaliculi of the right eye, such a device can be positioned in the inferior and superior canaliculus of the left eye, in lieu of or in addition to placement of a bicanalicular stent 100 in the right eye.

Figure 2C:
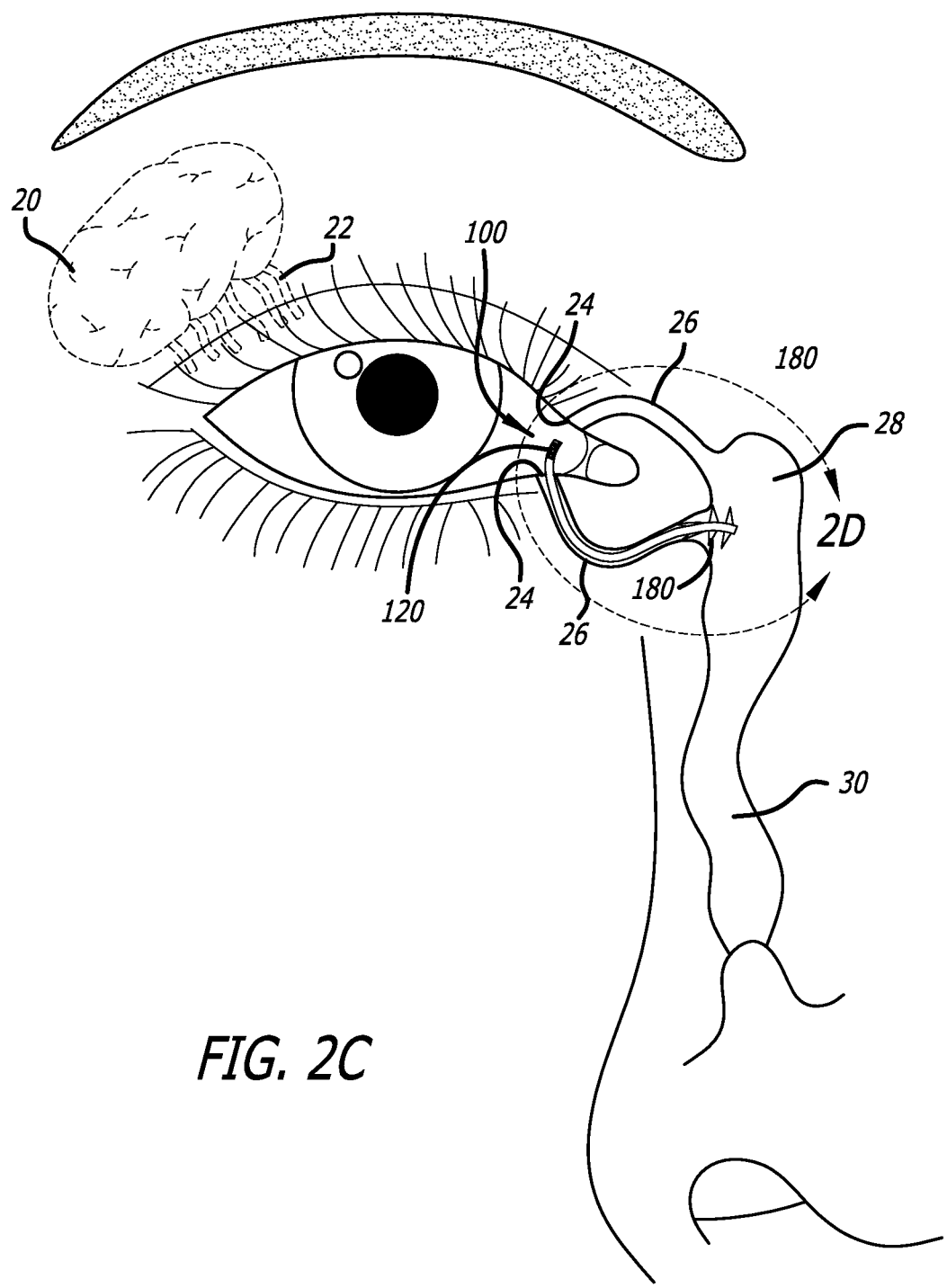
Figure 2D:
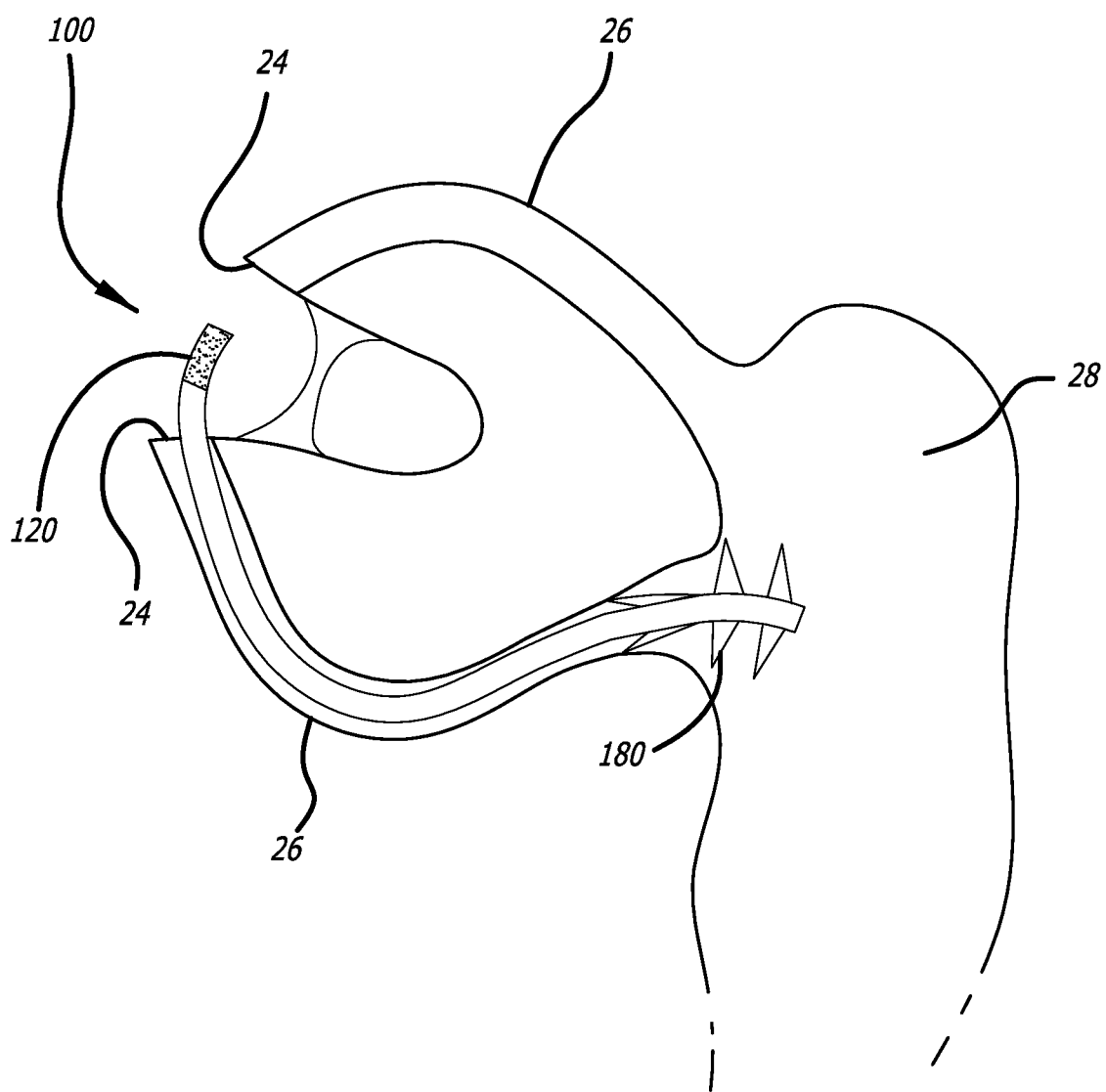

Referring to FIG. 2C-D, the same procedure is used as described for FIG. 2-A-B, except that a unicanalicular stent 100 is position in the inferior canaliculus 26. Although FIG. 2C-D show positioning in an inferior canaliculus of the right eye, such a device can be positioned in the superior canaliculus of the right eye or the inferior or superior canaliculus of the left eye.

Figure 2E:
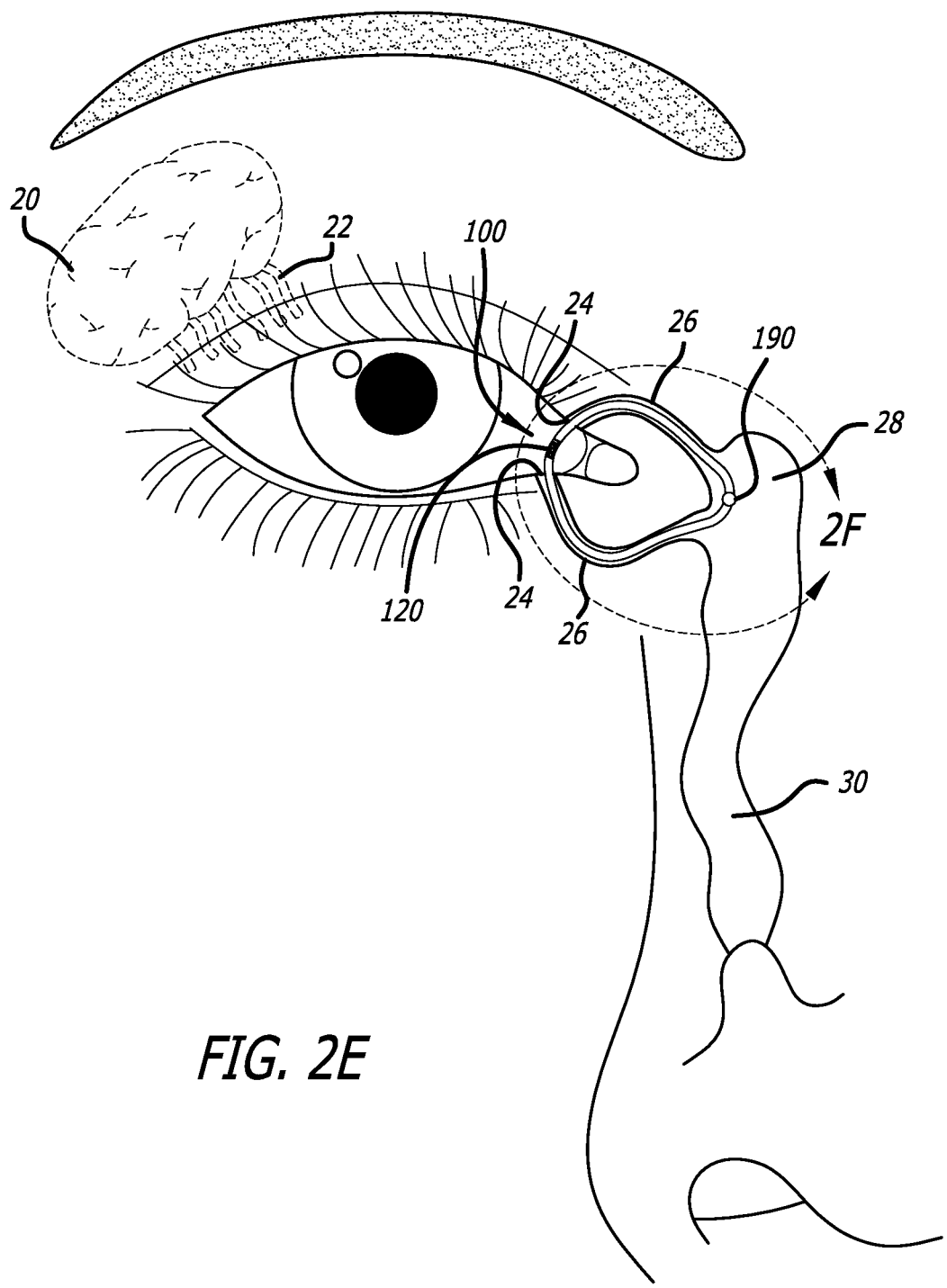
Figure 2F:
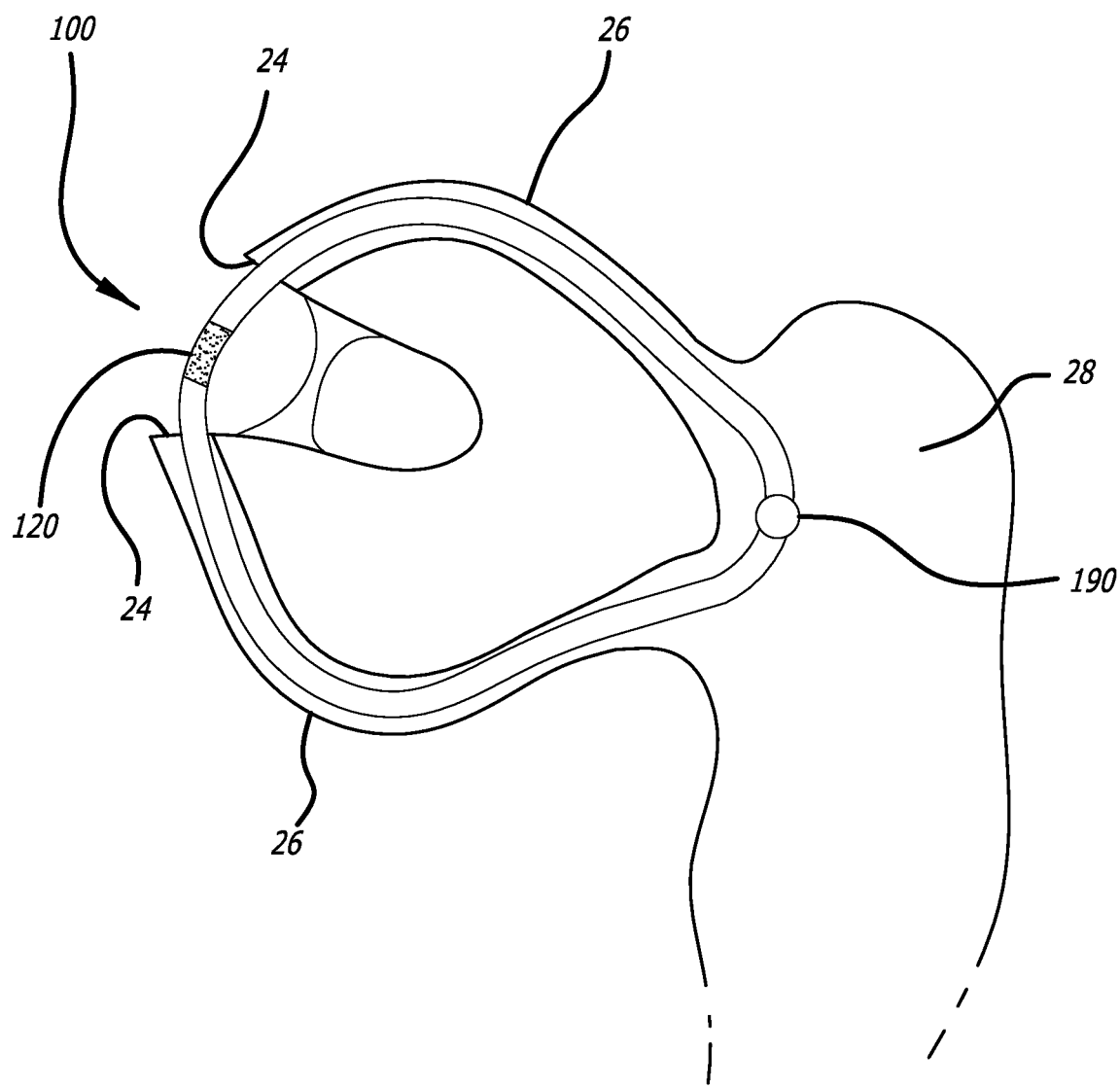

Referring to FIGS. 2E-F and using a method of treating glaucoma as an example, a patient will be placed at slit lamp after applying topical anesthetic eye drops (tetracaine) in each eye. A standard punctal dilator will then be manipulated by physician to dilate punctum to about 0.8 mm. This will be done to both the superior and inferior punctum 24. A small amount of lubricant, such as, e.g., CELLUVISC®, can be applied to tip of a bicanalicular stent 100 adjacent to attachment points comprising magnetic connector 190 to facilitate introduction of device. Either using small forceps holding distal end of tube (about 3.0 mm to about 4.0 mm from end perpendicular to bicanalicular stent 100 either end (superior or inferior), the distal end of bicanalicular stent 100 can be advanced into punctum 24 then ampulla and then forward into a canaliculus 26 so that first magnetic connector 190 enters lacrimal sac cavity 28. This can be similarity done with the metal stylet which should also provide a firm stop when touching opposite side of lacrimal sac 28. Gentle counter traction can then take place with forceps to ensure proper fixation of bicanalicular stent 100 in lacrimal sac 28. The same procedure is then carried out with the other end of bicanalicular stent 100 through the other punctum, ampulla, and canaliculus so that second magnetic connector 190 enters lacrimal sac cavity 28. Once both first and second magnetic connector 190 are positioned in lacrimal sac 28, magnetic attraction with connect first and second magnetic connector 190 to form a loop that secures bicanalicular stent 100 in place. Although FIG. 2E-F show positioning of a bicanalicular stent 100 in the inferior and superior canaliculi of the right eye, such a device can be positioned in the inferior and superior canaliculus of the left eye, in lieu of or in addition to placement of a bicanalicular stent 100 in the right eye.

Aspects of the present specification disclose methods and uses of treating an individual using a self-retaining canaliculus device disclosed herein. In aspects, the treatment is for an eye disorder or condition including, without limitation, glaucoma. Glaucoma In other aspects, the treatment is for an eye disorder or condition. Examples of a nasal disorder or condition include, without limitation, inflammation of the distal nasal lacrimal duct system and allergic rhinitis.

Glaucoma is a group of eye disorders that have few symptoms in their early stages, but eventually leads to damage of the optic nerve (the bundle of nerve fibers that carries information from the eye to the brain), which can then lead to vision loss or complete blindness. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. Public health figures estimate that 2.5 million Americans manifest ocular hypertension. Glaucoma costs the US economy $2.86 billion every year in direct costs and productivity losses. Currently, there is no cure for glaucoma, however, through early diagnosis and treatment, the disease can be controlled before vison loss or blindness occurs.

Most medications for the treatment of glaucoma are ophthalmic formulations that are administered as drops once or several times daily. Several published studies emphasize that the medicinal compliance among glaucoma patients is poor, and one study demonstrated that 25% of glaucoma patients took less than 75% of their prescribed doses and almost 20% of patients took less than 50% of their doses, which may lead to significantly reduced efficacy of the medications and accelerated loss of vision. One complication with glaucoma treatment compliance is getting the drop to the correct spot on the eye, as patients with glaucoma are often unable to see well enough to tell if the drop is centered over their eye. A second complication is applying the correct amount of pressure to the bottle to release the drop, as many patients, especially those with arthritis, find it difficult to squeeze a small bottle carefully. Finally, many patients find it difficult to hold the eyelid open during application of the drop, as many patients are simply unable to hold open their lids due to coordination or morbidity problems, or reflex blinking. Consequently, most of the drug may be wasted with less than ideal amounts delivered to the eye.

In various embodiments, a canalicular stent disclosed herein will be used for the treatment of glaucoma and will provide for the extended release of latanoprost (0.005%). In various embodiments, a canalicular stent disclosed herein will be used for the treatment of glaucoma and will provide for the extended release of RHOPRESSAR, netarsudil 0.02%) (Aerie Pharmaceuticals). In various embodiments, a canalicular stent disclosed herein will be used for the treatment of glaucoma and will provide for the extended release of RHOPRESSA®, netarsudil 0.02%) (Aerie Pharmaceuticals).

In various embodiments, a canalicular stent disclosed herein will be used for the treatment of glaucoma and will provide for the extended release of latanoprost (0.005%) in combination therapy with other another therapeutic agent capable of reducing intraocular pressure in the eye. In one embodiment, a canalicular stent disclosed herein will be used for the treatment of glaucoma and will provide for the extended release of latanoprost (0.005%) in combination therapy with RHOPRESSA®, netarsudil 0.02%) (Aerie Pharmaceuticals). In one embodiment, a canalicular stent disclosed herein will be used for the treatment of glaucoma and will provide for the extended release of latanoprost (0.005%) in combination therapy with ROCLATAN® (Aerie Pharmaceuticals).

Aspects of the present specification can also be described as follows:

1. A self-retaining implantable drug delivery comprising: a) a stent portion having a first distal end, a second distal end, and an elongated body between the first distal end and the second distal end; b) one or more drug depots including one or more therapeutic agents; and c) one or more anchors and/or one or more attachment points.
2. The device according to embodiment 1, wherein the one or more drug depots are located at a central portion of the elongated body of the stent portion.
3. The device according to embodiment 1 or 2, wherein the one or more drug depots are located at the first distal end, the second distal end or both the first and second distal ends of the stent portion.
4. The device according to any one of embodiments 1-3, wherein the one or more drug depot further comprises a polymer matrix and coating layer.
5. The device according to embodiment 4, wherein the coating layer is a metallic material.
6. The device according to embodiment 5, wherein the metallic material includes platinum or titanium.
7. The device according to embodiment 4, wherein the coating layer is a polymer.
8. The device according to embodiment 7, wherein the polymer includes a poly(p-xylylene) polymer.
9. The device according to any one of embodiments 1-8, wherein the one or more drug depots are a controlled-release formulation.
10. The device according to embodiment 9, wherein the controlled-release formulation is a sustained-release formulation or an extended release formulation.
11. The device according to embodiment 9 or 10, wherein the controlled-release formulation exhibits zero-order release kinetics
12. The device according to any one of embodiments 1-11, wherein the stent has 0.5 mm to 0.7 mm outside diameter and 0.2 mm to 0.4 mm inside diameter.
13. The device according to any one of embodiments 1-12, wherein the stent has a length of 10 mm to 50 mm.
14. The device according to any one of embodiments 1-13, wherein the one or more anchors are flexible winglets.
15. The device according to any one of embodiments 1-14, wherein the one or more attachment points are a pair of hooks, a hook and eyelet pair, Velcro, male and female connectors, and magnetic connectors
16. The device according to any one of embodiments 1-15, wherein the flexible winglet is 1.0 mm to 3.0 mm in length.
17. The device according to any one of embodiments 1-16, further comprises a biosensor capable of detecting and monitoring properties of a bodily fluid from the eye and/or intraocular pressure (IOP).
18. A self-retaining bicanalicular device comprising: a) a stent portion having a first distal end, a second distal end, and an elongated body between the first distal end and the second distal end; b) one or more drug depots including one or more therapeutic agents, the one or more drug depots being centrally located with respect to the elongated body; and c) one or more anchors and/or one or more attachment points.
19. A self-retaining bicanalicular device comprising: a) a stent portion having a first distal end, a second distal end, and an elongated body between the first distal end and the second distal end; the first distal end comprising one or more anchors and/or one or more attachment points and the second distal end comprising one or more anchors and/or one or more attachment points; and b) one or more drug depots including one or more therapeutic agents, the one or more drug depots being centrally located with respect to the elongated body; and
20. A self-retaining unicanalicular device comprising: a) a stent portion having a first distal end, a second distal end, and an elongated body between the first distal end and the second distal end; the first distal end comprising one or more anchors and/or one or more attachment points; and b) one or more drug depots including one or more therapeutic agents, the one or more drug depots being located at the second distal end of the stent portion.
21. A kit comprising the device as defined in any one of embodiments 1-20.
22. The kit of embodiment 21, further comprises metallic stylets that facilitate insertion and placement of a self-retaining stent.
23. A controlled-release drug depot comprising: a) a polymer matrix comprising one or more therapeutic drugs; and b) a coating layer on an outer surface of the polymer matrix, the polymer layer optionally having openings; wherein the one or more therapeutic drugs are released with approximate zero order kinetics.
24. A controlled-release drug depot comprising: a) a polymer matrix comprising one or more therapeutic drugs; and b) a coating layer on an outer surface of the polymer matrix, the polymer layer optionally having openings; wherein the one or more therapeutic drugs are released over period of time of at least one week and wherein the release rate approximates zero order kinetics.
25. A controlled-release drug depot comprising: a) a polymer matrix comprising one or more therapeutic drugs; and b) a coating layer on an outer surface of the polymer matrix, the polymer layer optionally having openings; wherein the one or more therapeutic drugs are released over period of time of at least one week and wherein the release rate approximates zero order kinetics.
26. The device according to any one of embodiments 23-25, wherein the controlled-release formulation is a sustained-release formulation or an extended release formulation.
27. The device according to any one of embodiments 23-26, wherein the layer is a metallic material.
28. The device according to embodiment 27, wherein the metallic material includes platinum or titanium.
29. The device according to any one of embodiments 23-25, wherein the layer is a polymer.
30. The device according to embodiment 29, wherein the polymer includes a poly(p-xylylene) polymer.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the stents, kit devices, or methods and uses disclosed herein.

Example 1

To test the loading capacity of a silicone elastomer polymer matrix for a prostaglandin analogue, polymer matrix with different amounts and types of a prostaglandin analogue were made and the physical and mechanical properties of the resulting polymerized drug-loaded matrix were characterized (Tables 1-3). These polymer matrix test samples were made by mixing together a prostaglandin analogue, a liquid cyclic vinyl siloxane elastomer, a cross-linker, and a catalyst using a high-speed mixer and then heated the capped container at 70° C. for 24 hours to cure the mixture. A filler, such as a fumed silica, was also used to provide sufficient mechanical strength to the polymerized matrix. In addition, an inhibitor was used to slow the crosslinking reaction to a workable rate. The resulting thin-disc-shaped drug-loaded polymer matrix was allowed to cool to room temperature and then placed in 4° C. for 24 hours to increase stiffness of the material. The physical appearance of each drug-loaded polymer matrix test sample was examined visually and its mechanical properties analyzed using a durometer.

TABLE 1

Travoprost-Loaded Silicone Polymer Matrix Test Samples

| Component | 1 | 2 | 3 | 4 | 5 | 6 | 7 |
|---|---|---|---|---|---|---|---|
| Travoprost | 1% | 2.5% | 5% | 10% | 12.5% | 15% | 20% |
| Latanoprost | — | — | — | — | — | — | — |
| Bimatoprost | — | — | — | — | — | — | — |
| Silicone elastomer | 99% | 97.5% | 95% | 90% | 87.5% | 85% | 80% |
| Durometer Shore | D 22 | D 23 | OO 66 | D 27 | D 25 | OO 50 | D 22 |

Nusil Med 4-4220 using a 1:1 mixture of Part A and Part B.

TABLE 2

Bimatoprost-Loaded Silicone Polymer Matrix Test Samples

| Component | 8 | 9 | 10 | 11 | 12 | 13 |
|---|---|---|---|---|---|---|
| Travoprost | — | — | — | — | — | — |
| Latanoprost | — | — | — | — | — | — |
| Bimatoprost | 1% | 2.5% | 5% | 8.3% | 15% | 20% |
| Silicone elastomer | 99% | 97.5% | 95% | 91.7% | 85% | 80% |
| Durometer Shore | D 24 | D 25 | OO 78 | D 28 | OO 84 | OO 78 |

Nusil Med 4-4220 using a 1:1 mixture of Part A and Part B.

TABLE 3

Latanoprost-Loaded Silicone Polymer Matrix Test Samples

| Component | 14 | 15 | 16 | 17 | 18 |
|---|---|---|---|---|---|
| Travoprost | — | — | — | — | — |
| Latanoprost | 5% | 10% | 15% | 20% | 25% |
| Bimatoprost | — | — | — | — | — |
| Silicone elastomer | 95% | 90% | 85% | 80% | 75% |
| Durometer Shore | ND | ND | ND | ND | ND |

Nusil Med 4-4220 using a 1:1 mixture of Part A and Part B.
ND, Not determined.

Examination of the silicone polymer matrix test samples containing travoprost indicated that the 15% and 20% test samples exhibited more elasticity but had surfaces with tacky attributes and a consistency that was not fully homogeneous. These data suggest that Traveprest travoprost in an amount of 15% or more would not produce a satisfactory drug-loaded silicone polymer matrix.

With respect to the bimatoprost, initial observations indicated that test samples with 15% or 20% of this prostaglandin analogue were difficult to mix in the liquid siloxane elastomer. Furthermore, examination of the silicone polymer matrix test samples containing bimatoprost indicated that the 20% test sample was brittle and contained clumps of unincorporated components from the mixture. These data suggest that bimatoprost in an amount of 20% or more would not produce a satisfactory drug-loaded silicone polymer matrix.

Examination of the silicone polymer matrix test samples containing latanoprost indicated that the 25% test sample exhibited more elasticity but had a surface with tacky attributes and a consistency that was not fully homogeneous. These data suggest that-latanoprost in an amount of 25% or more would not produce a satisfactory drug-loaded silicone polymer matrix.

Example 2

To test the controlled release properties of the disclosed drug-loaded silicone polymer matrices, the effects of a coating were examined. In these experiments, test samples were made as described in Example 1 to produce thin-disc-shaped drug-loaded polymer matrix. From this material, test samples were prepared by 1) cutting out rectangular polygons of about 3 mm length, about 1 mm width and about 1 mm height were cut from polymerized drug-loaded material; or 2) cutting out cylindrical plugs of about 3 mm length and having a diameter of about 0.5 mm to about 1 mm. The weight of the test samples was in the range of about 0.1 mg to about 4 mg.

These cut test samples were then coated using one of three procedures. Cut test samples were coated with a polymer like poly(p-xylylene) (parylene) to a thickness of about 0.10 μm to about 0.95 μm using a vapor phase deposition procedure. Similarly, cut test samples were coated with a metal like titanium to a thickness of about 0.10 μm to about 0.95 μm using a vapor phase deposition procedure. Alternatively, cut test samples were physically wrapped with a tape like polytetrafluoroethylene tape and sealed using cyanoacrylate adhesive.

The presence of opening in a coated test sample was also examined. In these experiments, coated test samples were punctured to produce opening through the coating layer. From one to four openings were made using an 18G, 23G, 27G or 31G needle. Two types of opening were produced 1) surface pores which created openings only through the coating layer but left the polymer matrix intact; and 2) depot channels which created a tunnel through the entire coated test sample from one end to the other end.

To examine the drug release properties of a test sample, each sample was placed in 2 mL Eppendorf tube containing 1.5 mL of Phosphate Buffered Saline, pH 7.4 (PBS). These tubes were slowly rocked at 37° C. in an incubator. At given time points the PBS was completely removed from the tube and refilled with fresh PBS. An aliquot of the removed PBS was then analyzed by reversed phase HPLC (RPHPLC) to determine the amount of drug released from the test sample during the incubation period. In these experiments, a 10 μL injection of the test sample aliquot was run on an Agilent 1260 Infinity in a reverse phase isocratic mode using UV detection at 210 nm. The column was a Hypersil GOLD™ Phenyl column, (Dim. (mm) 250×4.6) and the mobile phase was a 1:1 mixture of acetonitrile to aqueous buffer (comprising HPLC grade water mixed with 5 mM ammonium acetate and 0.02% formic acid). The flow rate was 1.2 mL/min and column temperature was 22° C. Peak detection and quantitation were determined by establishing a calibration curve using known amounts of each drug tested and the amount of drug present in the test sample aliquot interpolated from this calibration curve using ChemStation software.

Figure 5:
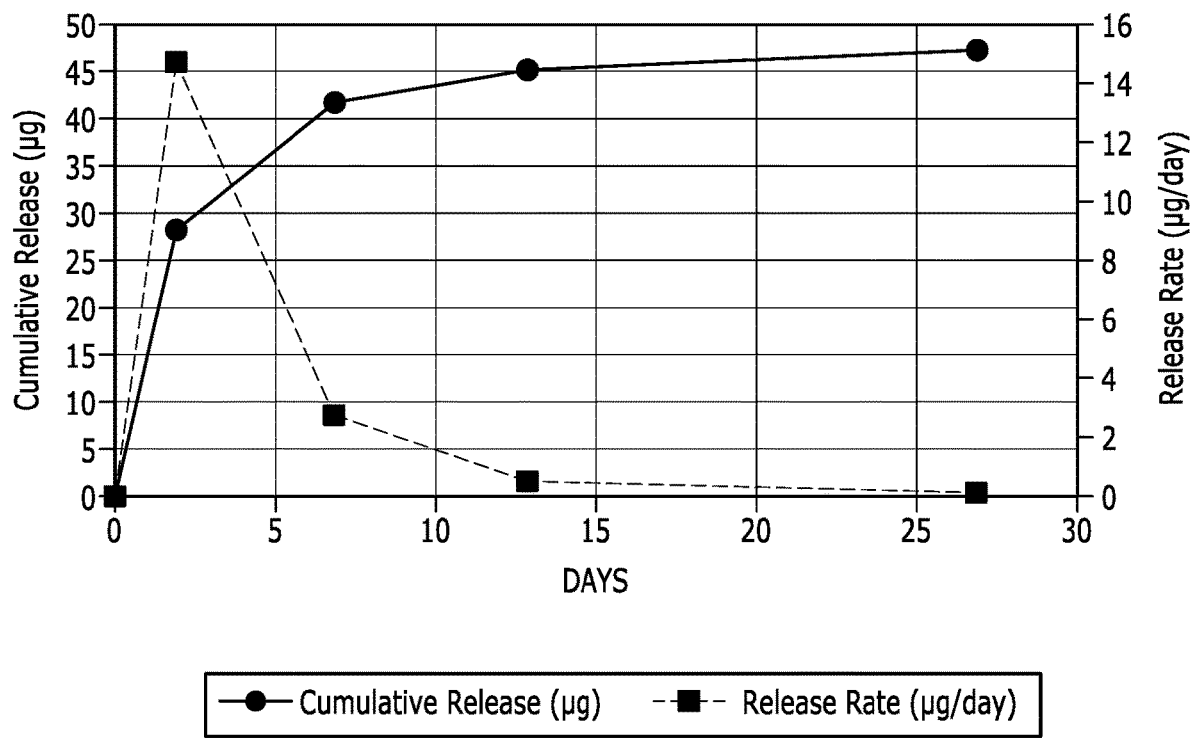
FIG. 5 shows a release profile of latanoprost from an uncoated silicone polymer matrix disclosed herein over the course of about 26 days with the left y-axis showing cumulative amount release of latanoprost (μg) and the right y-axis showing a release rate of latanoprost (μg/day).

An uncoated drug-loaded silicone polymer matrix disclosed herein exhibits an immediate, curvilinear/asymptotic release of drug that rapidly plateaus. Table 4 shows these findings. As exemplified in FIG. 5, an uncoated silicone polymer matrix, in this case loaded with 10% latanoprost, shows a rapid release of the drug over the first five days, which then tapers off and by day 12 shows no further significant release of latanoprost. Since a goal of this work was to develop a drug-loaded silicone polymer matrix exhibiting zero order release kinetics, coated matrices were examined.

TABLE 4

| Loading (A %) | Bimatoprost | Travoprost |
| --- | --- | --- |
| 1.0 | 0.204 ± 0.035 | 0.071 ± 0.001 |
| 2.5 | 0.387 ± 0.009 | 0.388 ± 0.046 |
| 5.0 | 1.680 ± 0.232 | 1.097 ± 0.218 |
| 10 | 2.327 ± 0.252 | 15.821 ± 4.141 |

Initial analysis indicated that coating a drug-loaded silicone polymer matrix with thin coatings of titanium did not inhibit the release of drug relative to uncoated control samples. These results suggest that metal coating may not be a suitable coating layer to achieve a controlled release of a drug-loaded silicone matrix as disclosed herein. On the other hand, coating a drug-loaded silicone polymer matrix with polytetrafluoroethylene tape resulted in no release of drug even after two weeks of testing. Surprisingly, coating a drug-loaded silicone polymer matrix with poly(p-xylylene) (parylene) resulted in no release of drug even after two weeks of testing.

In an effort to achieve a controlled release of drug in a disclosed silicone polymer matrix, openings were created in the coated test samples. A range of needle gauges spanning 18G to 31G were tested (Table 5) to determine the most effective opening size. In these experiments, ink-soaked needles were used to puncture coated test samples and excess ink was removed using an absorbent cloth. The resulting opening was measured using a DinoLite digital microscope at 25× magnification following puncture by an ink-soaked needle. The "path" was defined as the ink filled line as viewed from the side. The "pore" was defined as the circular spot of ink as viewed from above. The results of opening measurements are shown in Table 5.

TABLE 5

Size Testing of Openings

| | Needle | | Opening | |
| --- | --- | --- | --- | --- |
| Gauge | Outer diameter (mm) | Inner diameter (mm) | Diameter (mm) | Path (mm) |
| 18 | 1.270 | 0.838 | 0.329 | 0.661 |
| 23 | 0.6414 | 0.337 | 0.226 | 0.180 |
| 27 | 0.4128 | 0.210 | 0.100 | 0.159 |

Is assessing the effects of surface pores versus depot channels, it was observed that test samples with surface pores exhibited a very low drug release rate, although such release did exhibit a zero-order release kinetics. For example, in one assay, a test sample containing 25% latanoprost and having four surface pores, released near zero order for a period of 42 days, with average rates spanning approximately 0.3 μg/day to 0.4 μg/day. However, following this six-week period, the rate of release dropped precipitously, and as of 140 days, only 2.2% of the total amount of drug has been released. In contrast, as discussed below, our analysis indicated that two openings using an 18 G needle to create depot channels provided the best results and lead to zero-order controlled drug release for periods of at least 3 months.

Figure 6:
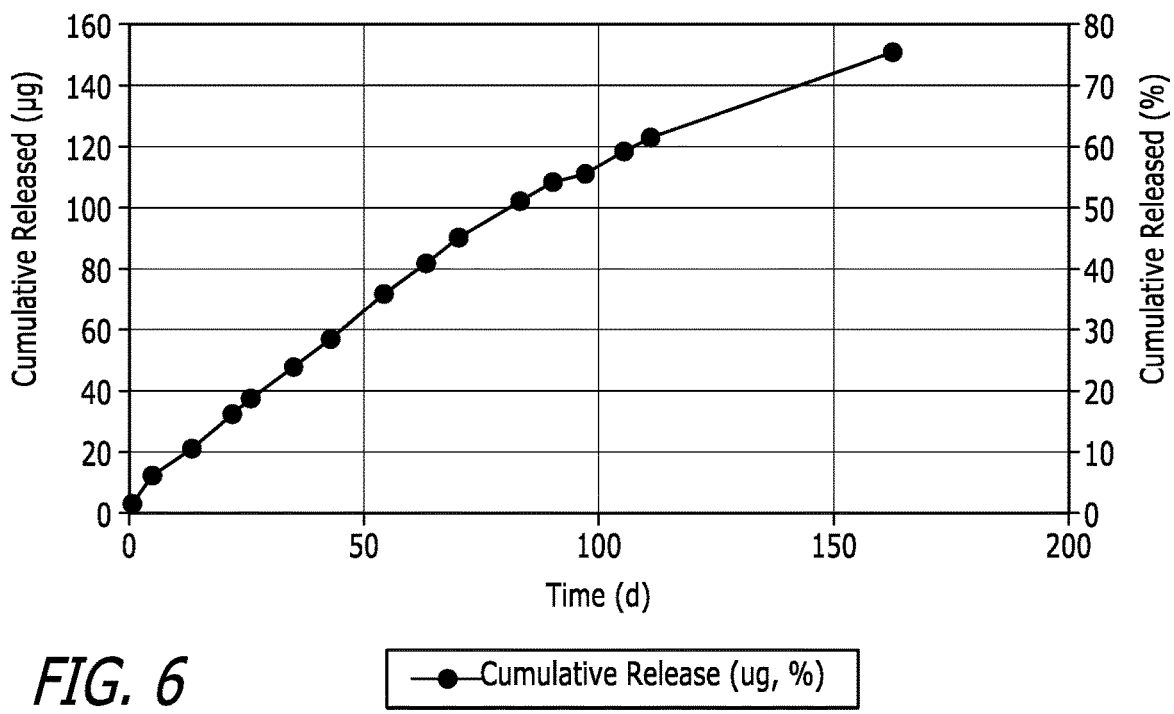
FIG. 6 shows a release profile of travoprost from a coated silicone polymer matrix disclosed herein over the course of about 160 days with the left y-axis showing cumulative amount release of travoprost (μg) and the right y-axis showing cumulative percent release of travoprost (%).
Figure 7:
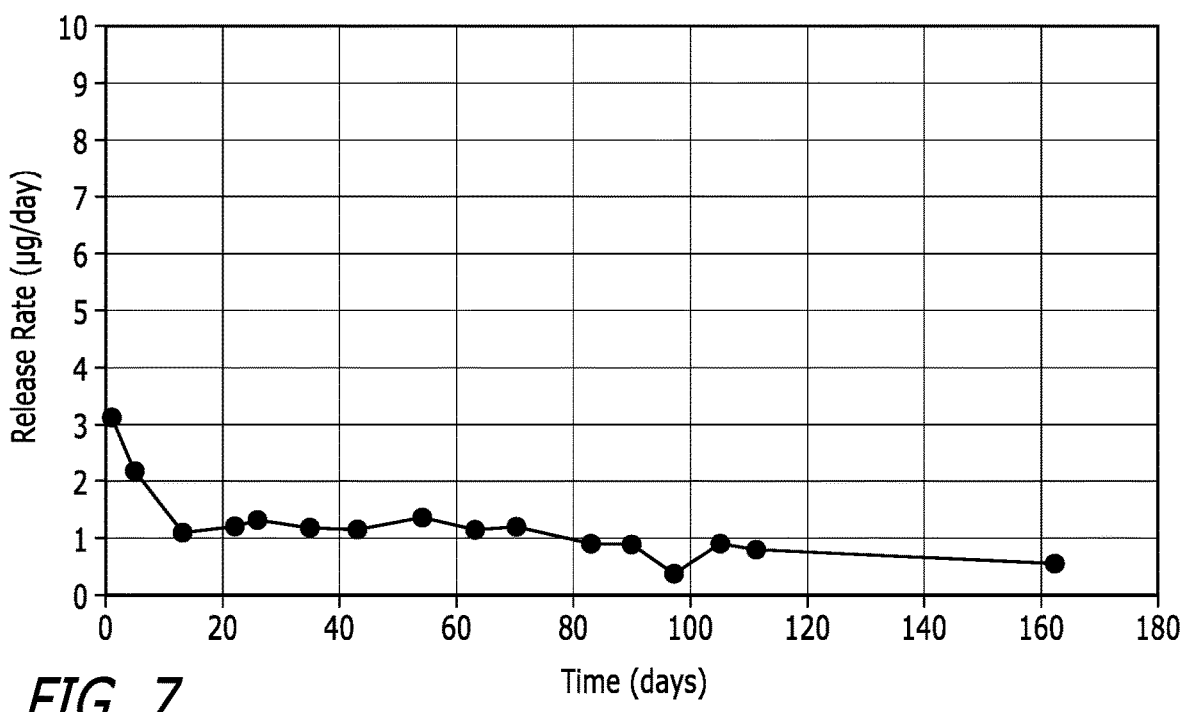
FIG. 7 shows a release rate of travoprost from a coated silicone polymer matrix disclosed herein over the course of about 160 days with the y-axis showing a release rate of travoprost (μg/day) and the right y-axis showing time (days).

In one controlled release experiment, the in vitro release of travoprost was examined using a coated silicone polymer matrix. In these experiments, a silicone polymer matrix cylindrical plug comprising 10% travoprost was made as described above in this example and coated with poly(p-xylylene) (parylene) to a thickness of about 0.68 μm. Two depot channels were made using an 18G needle. Release of travoprost was determined by RPHPLC analysis as described above and examined over the span of 162 days. The cumulative release of travoprost in amount and percentage of load in the silicone polymer matrix are shown in Table 6 and FIG. 6. The daily release rate over this time period is shown in Table 6 and FIG. 7.

TABLE 6

Travoprost Release Profile

| | Cumulative Release | | Daily Release |
| --- | --- | --- | --- |
| Time (days) | Amount (μg) | Amount (%) | Rate (μg/day) |
| 1 | 3.12 | 1.56 | 3.12 |
| 5 | 11.96 | 5.96 | 2.21 |
| 13 | 21.20 | 10.57 | 1.15 |
| 22 | 32.17 | 16.03 | 1.29 |
| 26 | 37.39 | 18.64 | 1.30 |
| 35 | 47.88 | 23.87 | 1.16 |
| 43 | 57.12 | 28.47 | 1.15 |
| 54 | 71.99 | 35.88 | 1.35 |
| 63 | 82.39 | 41.07 | 1.16 |
| 70 | 90.80 | 45.26 | 1.20 |
| 83 | 102.51 | 51.10 | 0.900 |
| 90 | 108.68 | 54.18 | 0.882 |
| 97 | 111.39 | 55.53 | 0.387 |
| 105 | 118.53 | 59.08 | 0.891 |
| 111 | 123.32 | 61.47 | 0.798 |
| 162 | 151.71 | 75.62 | 0.557 |

Figure 8:
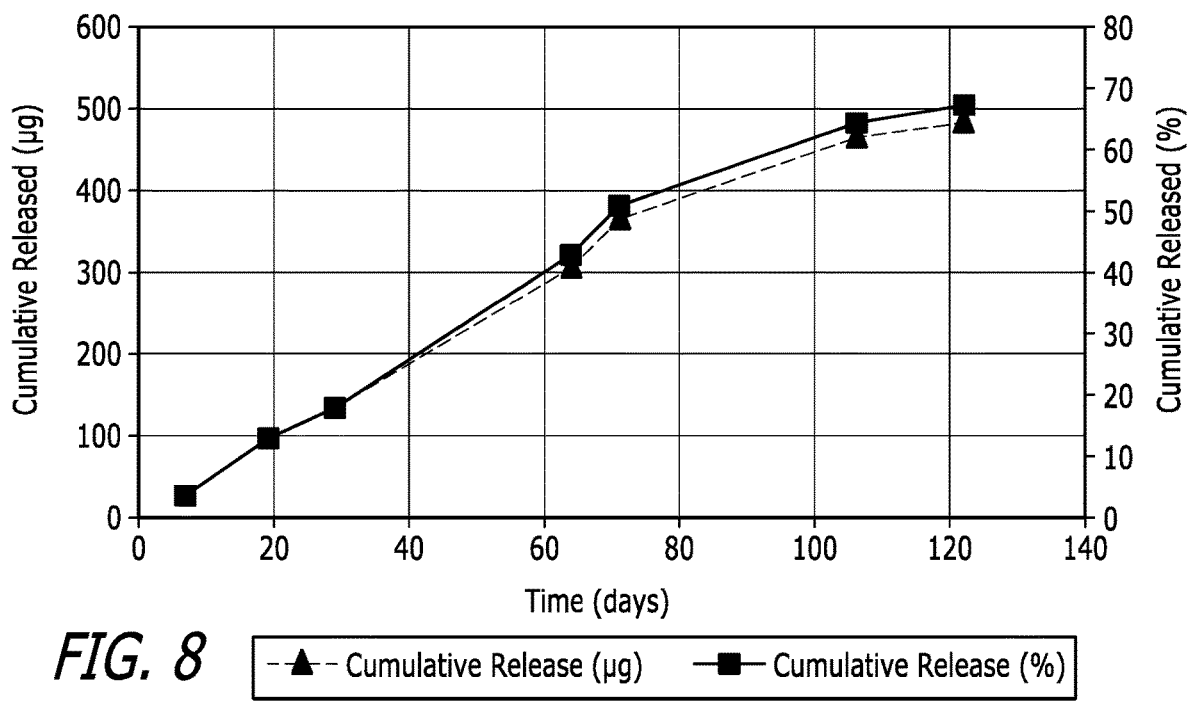
FIG. 8 shows a release profile of latanoprost from a coated silicone polymer matrix disclosed herein over the course of about 120 days with the left y-axis showing cumulative amount release of latanoprost (μg) and the right y-axis showing cumulative percent release of latanoprost (%).
Figure 9:
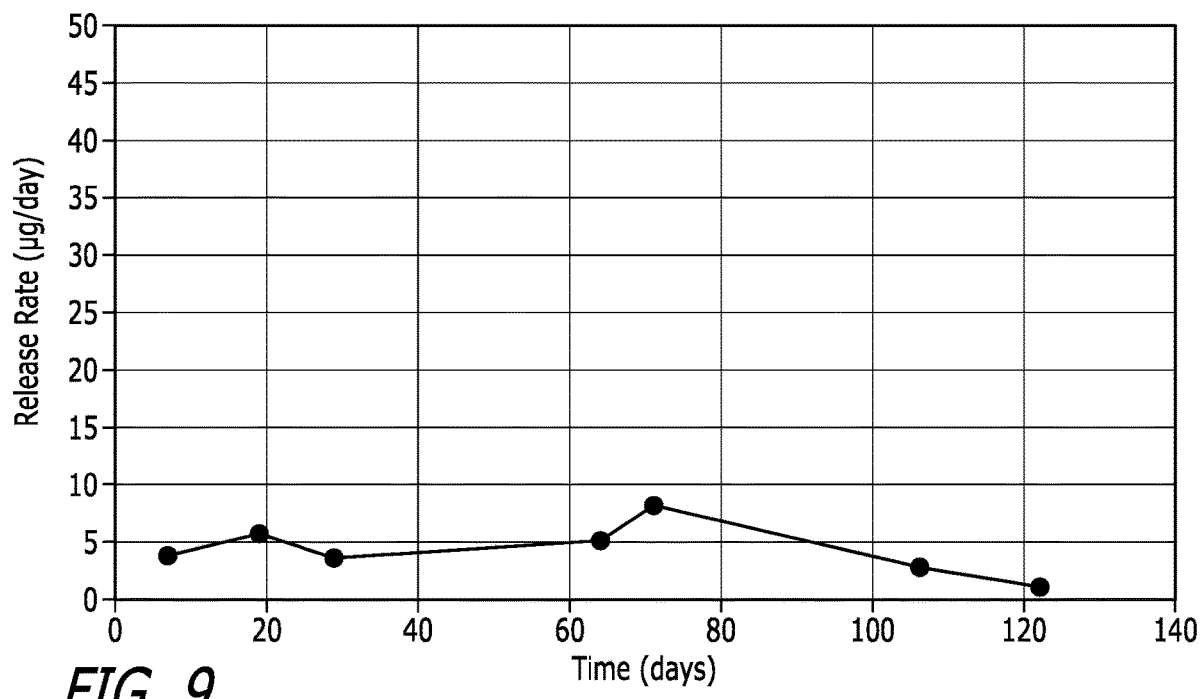
FIG. 9 shows a release rate of latanoprost from a coated silicone polymer matrix t disclosed herein over the course of about 120 days with the y-axis showing a release rate of latanoprost (μg/day) and the right y-axis showing time (days).

In one controlled release experiment, the in vitro release of latanoprost was examined using a coated silicone polymer matrix. In these experiments, a silicone polymer matrix cylindrical plug comprising 25% latanoprost was made as described above in this example and coated with PTFE Thread Seal Tape. Two depot channels were made using an 18G needle. Release of latanoprost was determined by RPHPLC analysis as described above and examined over the span of 120 days. The cumulative release of latanoprost in amount and percentage of load in the silicone polymer matrix are shown in Table 7 and FIG. 8. The daily release rate over this time period is shown in Table 7 and FIG. 9.

TABLE 7

Latanoprost Release Profile

| Time (days) | Cumulative Release | | Daily Release |
| | Amount (µg) | Amount (%) | Rate (µg/day) |
| --- | --- | --- | --- |
| 7 | 27.03 | 3.74 | 3.86 |
| 19 | 95.25 | 13.17 | 5.68 |
| 29 | 131.29 | 18.15 | 3.60 |
| 64 | 310.15 | 42.88 | 5.11 |
| 71 | 367.07 | 50.75 | 8.13 |
| 106 | 465.76 | 64.40 | 2.82 |
| 122 | 484.68 | 67.01 | 1.18 |

Figure 10:
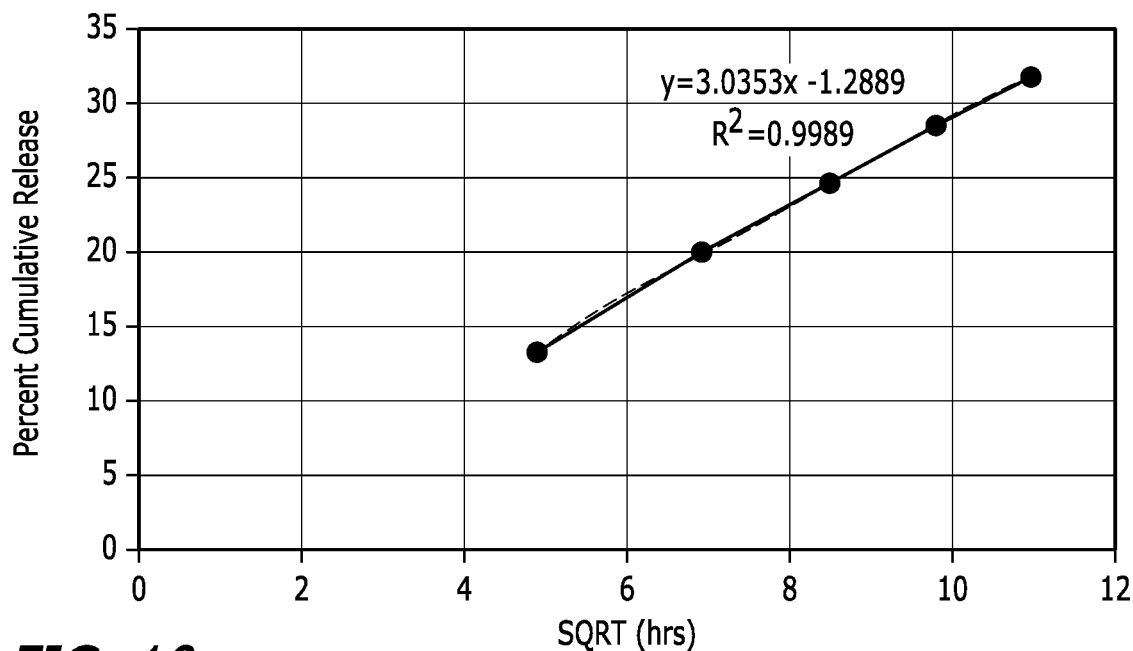
FIG. 10 shows a Higuchi Plot of latanoprost from a coated silicone polymer matrix disclosed herein.

In order to ascertain whether the mechanism of drug release was based on diffusion, data obtained from various coated silicone polymer matrices were analyzed using the Higuchi equation. This analysis determines the degree of proportionality between the cumulative amount of drug released and the square root of time (SQRT). A straight line suggests that release of the drug from a delivery system is by a diffusion process based in the Fick's law (i.e., Fickian diffusion). As exemplified FIG. 10, data is plotted as the square root of time taken on the x-axis and the cumulative percentage of drug release on the y-axis. This analysis demonstrates that the release of latanoprost is linear (linear regression $r^2$ value of 0.983) and that a diffusion process based in the Fick's law is the mechanism of drug release. Furthermore, Table 8 shows linear regression calculations for various coated drug-loaded silicone polymer matrices as disclosed herein indicating that all exhibit a Fickian diffusion process as the mechanism of drug release.

TABLE 8

Higuchi Equation Analysis

| Drug Loading | Average Linear Regression $r^2$ Value | | |
| | Travoprost | Latanoprost | Bimatoprost |
| --- | --- | --- | --- |
| 1% | — | — | 0.992 |
| 2.5% | 0.976 | — | 0.995 |
| 5% | 0.972 | 0.964 | 0.997 |
| 10% | 0.941 | 0.983 | 0.988 |
| 15% | — | 0.990 | 0.994 |
| 20% | — | 0.990 | 0.972 |

Figure 11:
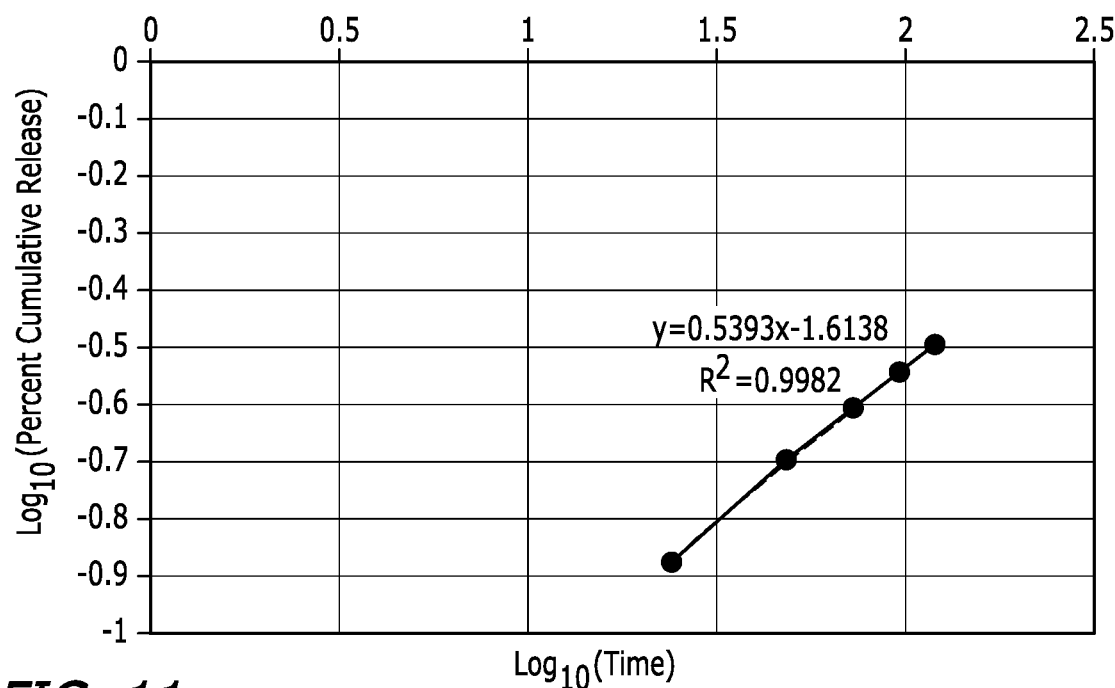
FIG. 11 shows log-log plots of release of latanoprost over time from a coated silicone polymer matrix disclosed herein with the y-axis plotting $Log_{10}$ (cumulative percent release of latanoprost) and the x-axis plotting $log_{10}$ (time in hours).

To confirm the results obtained based on the Higuchi equation analysis, the data above was also analyzed using the Korsmeyer-Peppas plot, which evaluates the mechanism of drug release by plotting the log of percent drug released over the log time in hours. If n equals 0.45, then Fickian diffusion is indicated for a cylinder (0.42 for cylinder of low aspect ratio). If n is greater than 0.45 but less than 0.89, a non-Fickian or anomalous diffusion is indicated suggesting both diffusion and erosion are contributing to the controlled release rate. As exemplified FIG. 11, data is plotted as the log of cumulative percent drug released on the y-axis and the log time in hours on the x-axis. This analysis demonstrates that the release of latanoprost is linear (linear regression $r^2$ value of 0.998) and that a diffusion process based in the Fick's law is the mechanism of drug release. Furthermore, as shown in Table 9, most of the various coated drug-loaded silicone polymer matrices have n values that are consistent within error with a Fickian diffusion process as the mechanism of drug release.

TABLE 9

Korsmeyer-Peppas Analysis

| Drug Loading | Average n Values | | |
| | Travoprost | Latanoprost | Bimatoprost |
| --- | --- | --- | --- |
| 1% | — | — | 0.326± |
| 2.5% | 0.543± | — | 0.372± |
| 5% | 0.507± | 0.504± | 0.411± |
| 10% | 0.453± | 0.501± | 0.377± |
| 15% | — | 0.712± | 0.380± |
| 20% | — | 1.200± | 0.601± |
| Mean | 0.50 ± 0.09 | 0.57 ± 0.16 | 0.37 ± 0.08 |

Travoprost and latanoprost are oily liquids at room temperature whereas bimatoprost is a solid at room temperature. To determine whether the liquid versus solid transition phase of these drugs affects their release from the silicone polymer matrix, data was analyzed using an alternative plot based on the Higuchi equation where twice the drug loading value (2A) is plotted on the x-axis and the average slope of the plot of cumulative drug released squared versus time in hours (Q^2/T) is plotted on the x-axis. If the mechanism of drug release is based on Fickian diffusion, then a linear relationship should be observed for a solid drug formulated in a monolithic dispersion and a curvilinear relationship should be observed for a liquid drug formulated in a monolithic dispersion.

TABLE 10

| Loading (A %) | Bimatoprost | Travoprost |
| --- | --- | --- |
| 1.0 | 0.204 ± 0.035 | 0.071 ± 0.001 |
| 2.5 | 0.387 ± 0.009 | 0.388 ± 0.046 |
| 5.0 | 1.680 ± 0.232 | 1.097 ± 0.218 |
| 10 | 2.327 ± 0.252 | 15.821 ± 4.141 |

Figure 12:
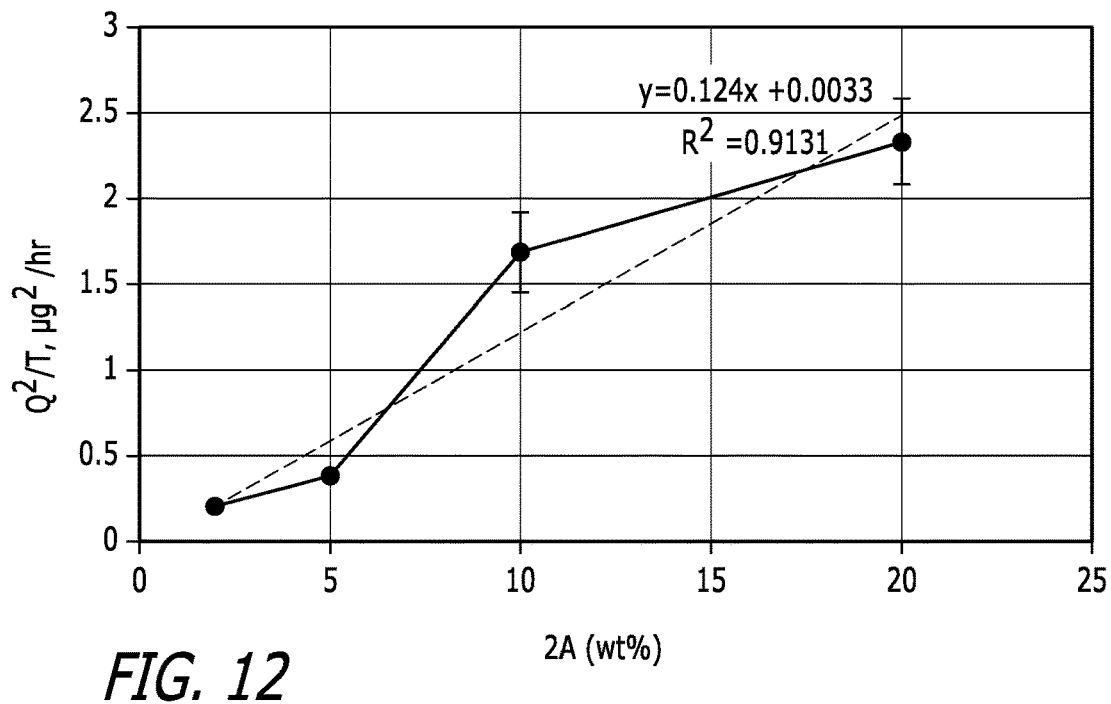
FIG. 12 shows a modified Higuchi Plot of bimatoprost from a coated silicone polymer matrix disclosed herein.
Figure 13:
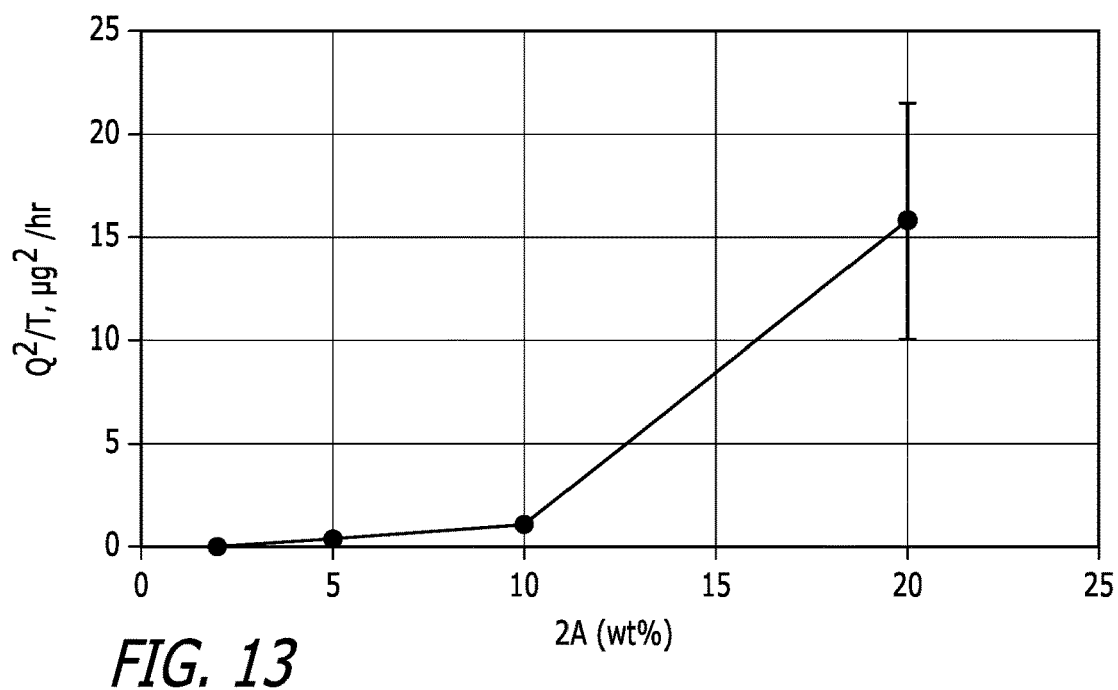
FIG. 13 shows a modified Higuchi Plot of travoprost from a coated silicone polymer matrix disclosed herein.

As shown in Table 10 and FIG. 12 silicone polymer matrices loaded with bimatoprost show a linear relationship whereas Table 10 and FIG. 13 show that silicone polymer matrices loaded with travoprost show a curvilinear relationship. It is theorized that deviation from the Higuchi concentration mechanism for travoprost is based on the tensile strength of the silicone polymer matrix. In essence the liquid dispersions of travoprost have a significant plasticizing effect. As the loading increases the polymer matrix becomes more flexible as a consequence of the increase in free volume of the system. Thus, at higher loading would enhance the initial release, and thus the plot curves upward at higher loading. As the release continues the matrix would become less flexible and at later times one would observe a less enhanced effect on the release. The solid drug bimatoprost would be expected to show a less pronounced plasticizing effect, but in general the modulus would increase with drug, becoming more rigid.

Example 3

The chemical stability of prostaglandin analogues was also examined. In these experiments, a prostaglandin analogue was incubated in phospho-buffered saline (PBS) at pH 4, 7 and 10 and at 4° C., 33° C. and 50° C. representing long term storage, eye temperature and accelerate temperature conditions respectively. Analyses were performed by RPHPLC as described in Example 2, noting any hydrolysis products formed. Unlike latanoprost, this examination found that travoprost and bimatoprost had the requisite stability with bimatoprost being the most stable. This stability is most likely due to the amide linkage in bimatoprost which is much more hydrolytically stable than the ester linkage in latanoprost and travoprost. It is not clear why travoprost was significantly more stable than latanoprost but it is theorized that the trifluoromethylphenoxy ring and the neighboring hydroxyl group would direct hydrolytic stability on the ester group.

Example 4

To manufacture a canalicular device disclosed herein, a drug-loaded silicone polymer matrix was made, e.g., as described in Example 2, having the shape of a cylinder with a length of about 3 mm and a diameter approximating the diameter of a stent. A stent was then spliced, and a silicone polymer matrix cylindrical plug was either molded directly in place by thinly coating the stent and plug components with unpolymerized silicone polymer and heated at 80° C. for 24 hours. Alternatively, the stent and plug components can be bonded together using a medical grade silicone adhesive.

In an alternative procedure, a hole is punched or drilled in a stent and the inner diameter of the stent is filled with a drug-loaded silicone polymer matrix as described in Example 1, except that the uncured mixture is deposited into the hole of the stent instead of a container.

Example 5

A central section of a self-retaining implantable drug delivery device disclosed herein was loaded with travoprost by cutting a 3 mm section of the device and then placed into 0.200 ml of hexanes for 3 hours. Following this period, the self-retaining implantable drug delivery device was placed immediately into 0.050 mL of a travoprost stock solution 25 mg/mL in ethanol and allowed to stand overnight. The following day, this section was washed sequentially by dipping into a water bath, followed by a 10% acetonitrile bath. It was dried at 80 C and set to release the following day. The section was allowed to release over a period of 38 days. The loading was determined to be approximately 13 mcg. The release followed a curvilinear/asymptotic profile where 50% was released between 6 to 7 days and 99% was released at 38 days. This release profile is predicted by the Higuchi mechanism. This type of loading procedure we term post loading.

The loaded section is coated with a poly(p-xylylene) polymer and two tiny holes are placed completely through the section. The section is then molded together with the two flanking sections of the stent to form the final product. The release from this modified stent follows a near zero order release in vitro and in vivo in preclinical animal models and clinical studies.

In this example the unmodified stent is post loaded in the following manner. A central portion of the stent is placed in contact with a 25 mg/mL travoprost solution and washed and dried as in the example above. The stent is coated with a poly(p-xylene) polymer such that the coating covers the loaded portion. Holes are placed through the loaded portion as in the example above to form the final product. The release follows the profile described in the example above. Alternatively, a thin barrier section is introduced next to both sides of the loaded section such that drug is impeded in flowing through the unloaded part of the stent and thus flows only through the holes. The barrier is made of drug impermeable materials such as polymers, metals or gases.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators-such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as "comprise" and "comprises", and equivalent open-ended transitional phrases thereof like "including," "containing" and "having", encompasses all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A controlled-release drug depot comprising:
   a) a polymer matrix comprising a silicone polymer matrix material and a prostaglandin analogue, wherein the prostaglandin analogue is present in an amount of from 1% to 25% of the total weight of the polymer matrix material;
   b) from one to five coating layers on an outer surface of the polymer matrix that form a drug impermeable membrane, the one to five coating layers having at least one coating layer comprising a poly(p-xylylene) polymer or a metallic material; and
   c) from one to five depot channels, wherein each of the one to five depot channels being a tunnel that entirely traversing thorough the polymer matrix and the one to five coating layers, and each of the one to five depot channels providing a controlled release of the prostaglandin analogue; and
   wherein the controlled-release drug depot is a sustained-release formulation that releases the prostaglandin analogue over a period of from 7 days to 90 days.

2. The controlled-release drug depot according to claim 1, wherein the prostaglandin analogue is selected from the group consisting of bimatoprost, latanoprost, tafluprost, and travoprost.

3. The controlled-release drug depot according to claim 1, wherein the prostaglandin analogue is present in an amount of from 5% to 25% of the total weight of the polymer matrix material.

4. The controlled-release drug depot according to claim 1, wherein the prostaglandin analogue is present in an amount of from 2.5% to 25% of the total weight of the polymer matrix material.

5. The controlled-release drug depot according to claim 1, wherein the at least one coating layer consists of a poly(p-xylylene) polymer.

6. The controlled-release drug depot according to claim 5, wherein each of the one to five coating layers consists of a poly(p-xylylene) polymer.

7. The controlled-release drug depot according to claim 1, wherein the at least one coating layer consists of a metallic material.

8. The controlled-release drug depot according to claim 7, wherein the metallic material is platinum or titanium.

9. The controlled-release drug depot according to claim 1, wherein the composition has from 1 to 3 coating layers.

10. The controlled-release drug depot according to claim 1, wherein the composition has from 2 to 5 coating layers.

11. The controlled-release drug depot according to claim 10, wherein the composition has a first coating layer consisting of a poly(p-xylylene) polymer and a second coating layer consisting of a metallic material.

12. The controlled-release drug depot according to claim 11, wherein the first coating layer consisting of a poly(p-xylylene) polymer is next to the polymer matrix and the second coating layer consisting of a metallic material is over the first coating layer.

13. The controlled-release drug depot according to claim 11, wherein the metallic material is platinum or titanium.

14. The controlled-release drug depot according to claim 1, wherein the polymer matrix is cylindrical and has an outer curved surface, wherein each of the one to five coating layers is also cylindrical and has curved surfaces, and wherein each of the one to five depot channels is provided orthogonally relative to each of the curved surfaces of the one to five coating layers and which exposes the polymer matrix.

15. The controlled-release drug depot according to claim 1 comprising from two to five depot channels.

16. The controlled-release drug depot according to claim 15 comprising from three to five depot channels.

17. The controlled-release drug depot according to claim 1, wherein the prostaglandin analogue is released over a period of from 30 days to 90 days.

18. The controlled-release drug depot according to claim 1, wherein the prostaglandin analogue is released over a period of from 60 days to 90 days.

19. The controlled-release drug depot according to claim 1, wherein the prostaglandin analogue is released over a period of from 7 days to 30 days.

* * * * *